(12) United States Patent
Kondo et al.

(10) Patent No.: US 11,000,196 B2
(45) Date of Patent: May 11, 2021

(54) PRESSURE PULSE WAVE MEASUREMENT APPARATUS AND BODILY INFORMATION MEASUREMENT APPARATUS

(71) Applicant: OMRON HEALTHCARE CO., LTD., Kyoto (JP)

(72) Inventors: Katsunori Kondo, Muko (JP); Toshihiko Ogura, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 335 days.

(21) Appl. No.: 16/027,867

(22) Filed: Jul. 5, 2018

(65) Prior Publication Data

US 2018/0325383 A1 Nov. 15, 2018

Related U.S. Application Data

(63) Continuation of application No. PCT/JP2016/083261, filed on Nov. 9, 2016.

(30) Foreign Application Priority Data

Jan. 8, 2016 (JP) .............................. JP2016-002445

(51) Int. Cl.
*A61B 5/022* (2006.01)
*A61B 5/00* (2006.01)
(Continued)

(52) U.S. Cl.
CPC .......... *A61B 5/022* (2013.01); *A61B 5/02116* (2013.01); *A61B 5/6824* (2013.01);
(Continued)

(58) Field of Classification Search
CPC ...... A61B 2562/0247; A61B 2562/046; G01L 27/005
(Continued)

(56) References Cited

U.S. PATENT DOCUMENTS 4,830,017 A 5/1989 Perry et al.
6,676,600 B1 * 1/2004 Conero .................... A61B 5/00
600/438
(Continued)

FOREIGN PATENT DOCUMENTS

CN 101703394 5/2010
CN 102292021 12/2011
(Continued)

OTHER PUBLICATIONS

Office Action dated May 25, 2020 in corresponding Chinese Patent Application No. 201680077954.X, with English Translation.
(Continued)

*Primary Examiner* — Daniel L Cerioni
*Assistant Examiner* — Deirdre M Willgohs
(74) *Attorney, Agent, or Firm* — Wenderoth, Lind & Ponack, L.L.P.

(57) ABSTRACT

A pressure pulse wave measurement apparatus includes: a sensor unit in which an element column including a plurality of pressure detection elements that are arranged side by side in one direction is formed; a pressing unit configured to press the sensor unit against a body surface of a living body; and a rotation control member configured to rotate the sensor unit about each of two axes that are orthogonal to a pressing direction of the pressing unit. The rotation control member includes a first member and a second member that are relatively rotated about a rotation axis extending in the pressing direction, and the first member and the second member both include a motion conversion mechanism for converting a rotational motion realized by the first member and the second member being relatively rotated, into a rotational motion of the sensor unit about each of the two axes.

13 Claims, 16 Drawing Sheets

(51) Int. Cl.
  *A61B 5/021* (2006.01)
  *G01L 27/00* (2006.01)
(52) U.S. Cl.
  CPC .......... *A61B 5/6885* (2013.01); *A61B 5/681* (2013.01); *A61B 2562/0247* (2013.01); *A61B 2562/046* (2013.01); *G01L 27/005* (2013.01)
(58) Field of Classification Search
  USPC ....................................................... 600/490
  See application file for complete search history.

(56) References Cited

U.S. PATENT DOCUMENTS

| | | | |
|---|---|---|---|
| 8,747,327 B2 * | 6/2014 | Kim | A61B 5/0225 600/493 |
| 2006/0184051 A1 | 8/2006 | Hempstead et al. | |
| 2011/0275946 A1 | 11/2011 | Ashida | |
| 2015/0182147 A1 | 7/2015 | Sato et al. | |

FOREIGN PATENT DOCUMENTS

| | | |
|---|---|---|
| EP | 0 330 434 | 8/1989 |
| JP | 1-209045 | 8/1989 |
| JP | 1-288228 | 11/1989 |
| JP | 2-1220 | 1/1990 |
| JP | 4-309772 | 11/1992 |
| JP | 5-20709 | 3/1993 |
| JP | 5-184548 | 7/1993 |
| JP | 2002-330932 | 11/2002 |
| JP | 2010-220948 | 10/2010 |
| JP | 2010-220949 | 10/2010 |

OTHER PUBLICATIONS

International Search Report, dated Jan. 24, 2017 in corresponding International Patent Application No. PCT/JP2016/083261.

* cited by examiner

PRESSURE PULSE WAVE MEASUREMENT APPARATUS AND BODILY INFORMATION MEASUREMENT APPARATUS

CROSS-REFERENCE TO RELATED APPLICATION(S)

This application is a continuation of PCT application No. PCT/JP2016/083261, which was filed on Nov. 9, 2016 based on Japanese Patent Application (No. 2016-002445) filed on Jan. 8, 2016, the contents of which are incorporated herein by reference.

BACKGROUND

Technical Field

The present invention relates to a pressure pulse wave measurement apparatus and a bodily information measurement apparatus.

Background Art

A bodily information measurement apparatus is known that can, in a state in which a pressure sensor is in direct contact with a body region under which an artery such as the radial artery of a wrist passes, measure bodily information such as pulse rate and blood pressure using information detected by the pressure sensor. In this bodily information measurement apparatus, the positional relationship between the pressure sensor and the artery affects the measurement accuracy of the bodily information. Therefore, configurations for adjusting the positional relationship between a body region and a pressure sensor have been proposed as shown in Patent Documents 1 to 6.

A bodily information measurement apparatus described in Patent Document 1 includes a sensor group including 6×7=42 sensors that are to be brought into contact with a body region, and includes a mechanism for manually adjusting the inclination of the sensor group in the artery direction such that favorable outputs of the sensors in the sensor group can be obtained.

A bodily information measurement apparatus described in Patent Document 2 includes a sensor group including 6×7=42 sensors that are to be brought into contact with a body region. In this bodily information measurement apparatus, the sensor group is divided into four areas such that the contact between the sensor group and the body region can follow the movement of a hand, and the bodily information measurement apparatus includes a mechanism according to which the heights of the respective divided areas can be adjusted.

In Patent Document 3, a bodily information measurement apparatus is disclosed that includes a pressure sensor that is to be brought into contact with a body region, and a drive unit that moves the pressure sensor in a direction that intersects an artery.

In Patent Document 4, a bodily information measurement apparatus is disclosed that includes a pressure sensor column that is to be brought into contact with a body region, and a drive unit that rotates the pressure sensor column in a plane that intersects the pressing direction of the pressure sensor column.

In Patent Documents 5 and 6, a bodily information measurement apparatus is disclosed that includes a pressing surface formed by a plurality of pressure sensor columns, which are arranged side by side, and that are to be brought into contact with a body region, and a drive unit that rotates the pressing surface about an axis that extends in a direction that is orthogonal to a direction in which the plurality of pressure sensor columns are arranged.

CITATION LIST

Patent Literature

Patent Document 1: JP 2010-220948A
Patent Document 2: JP 2010-220949A
Patent Document 3: JP H02-001220A
Patent Document 4: JP 2002-330932A
Patent Document 5: JP H01-288228A
Patent Document 6: JP H01-209045

In the apparatuses described in Patent Documents 1 and 2, although the state of contact between the sensor group and a body region can be changed, the state of contact changes so as to follow the shape of the wrist of a user, or the state of contact is manually changed. Therefore, it is not possible to perform positioning of the sensors with sufficient consideration given to the measurement accuracy of the bodily information.

The apparatuses described in Patent Documents 3 to 6 control the position of the pressure sensor such that the output of the pressure sensor becomes favorable, and therefore it is possible to perform positioning of the pressure sensor with consideration given to the measurement accuracy of the bodily information. However, in the case where the pressure sensor is pressed against a body region and the bodily information is calculated using a pressure pulse wave output from the pressure sensor in this state, it is envisioned that the position of the artery changes due to the pressing force. It is difficult for the apparatuses described in Patent Documents 3 to 6 to sufficiently follow such a change in position.

The present invention was made in view of the above-described circumstances and aims to provide a pressure pulse wave measurement apparatus in which the state of contact between a sensor unit, which is brought into contact with a body region for use, and the body region is flexibly changed so as to improve the accuracy in measuring a pressure pulse wave, and a bodily information measurement apparatus including this pressure pulse wave measurement apparatus.

SUMMARY

A pressure pulse wave measurement apparatus of the present invention includes: a sensor unit in which an element column including a plurality of pressure detection elements that are arranged side by side in one direction is formed; a pressing unit configured to press the sensor unit against a body surface of a living body; and a rotation control member configured to rotate the sensor unit about each of two axes that are orthogonal to a pressing direction of the pressing unit. The rotation control member includes a first member and a second member that are relatively rotated about a rotation axis extending in the pressing direction. The first member and the second member both include a motion conversion mechanism for converting a rotational motion realized by the first member and the second member being relatively rotated into a rotational motion of the sensor unit about each of the two axes.

DESCRIPTION OF EMBODIMENTS

Hereinafter, an embodiment of the present invention will be described with reference to the drawings.

Figure 1:
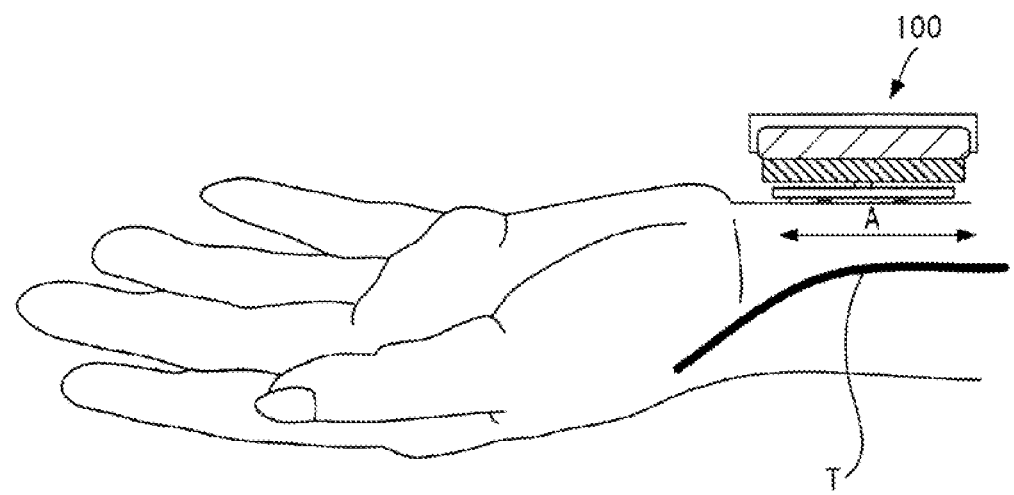
FIG. 1 is a diagram illustrating a state in which a pressure pulse wave measurement unit 100, which is one embodiment of the present invention and is to be mounted in a blood pressure measurement apparatus, is attached to a wrist.

FIG. 1 is a diagram illustrating a state in which a pressure pulse wave measurement unit 100, which is one embodiment of the present invention and is to be mounted in a blood pressure measurement apparatus, is attached to a wrist. The blood pressure measurement apparatus is used in a state of being attached by an unshown belt to a body region (user wrist in the example in FIG. 1) in which the artery (the radial artery T in the example in FIG. 1) that is the blood pressure measurement target exists under the body surface (skin). The pressure pulse wave measurement unit 100 constitutes a pressure pulse wave measurement apparatus.

Figure 2:
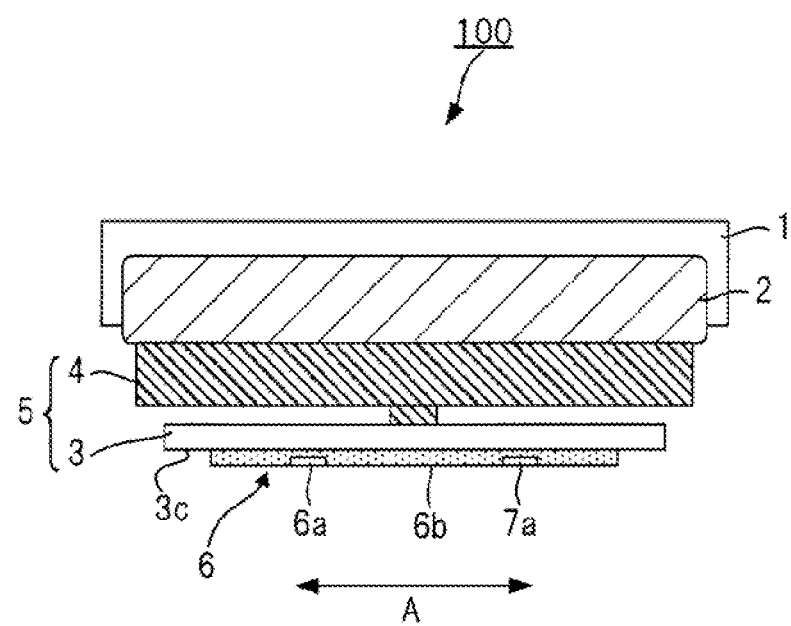
FIG. 2 is an enlarged view of the pressure pulse wave measurement unit 100 shown in FIG. 1.

FIG. 2 is an enlarged view of the pressure pulse wave measurement unit 100 shown in FIG. 1.

The pressure pulse wave measurement unit 100 includes a casing 1 that includes an air bladder 2, a rotation control member 5 fixed to the air bladder 2, and a sensor unit 6 fixed to the rotation control member 5.

The air bladder 2 moves the rotation control member 5 fixed to the air bladder 2 in an up-down direction in FIG. 2, as a result of the amount of air inside the air bladder 2 being controlled by an unshown pump.

The air bladder 2 moves the rotation control member 5 in a direction of approaching the body region (downward direction in FIG. 2) in a state in which the blood pressure measurement apparatus is attached to a wrist, and as a result, the air bladder 2 functions as a pressing unit that presses the sensor unit 6 fixed to the rotation control member 5 against the body surface of the body region. The pressing unit need only be a mechanism that can press the sensor unit 6 against a body surface, and is not limited to a mechanism that uses the air bladder.

In the attachment state shown in FIG. 1, a sensor surface 6b of the sensor unit 6 included in the pressure pulse wave measurement unit 100 comes into contact with the skin of the user wrist. As a result of the amount of air injected into the air bladder 2 being increased in this state, the pressure inside the air bladder 2 increases, and the rotation control member 5 and the sensor unit 6 are pressed toward the radial artery T of the wrist. In the following description, the pressing force of the sensor unit 6 applied to the radial artery T is assumed to be equivalent to the pressure inside the air bladder 2. The direction in which the rotation control member 5 and the sensor unit 6 are pressed by the air bladder 2 is referred to as a pressing direction.

The rotation control member 5 includes a fixed unit 4 fixed to the air bladder 2, and a sensor table 3 serving as a first member coupled to the fixed unit 4.

The sensor table 3 is a plate-shaped member including a sensor fixing surface 3c on which the sensor unit 6 is fixed. An end surface out of two end surfaces of the sensor table 3 in the pressing direction closer to the wrist, in the attachment state in FIG. 1, is the sensor fixing surface 3c.

The sensor unit 6 is fixed to the sensor fixing surface 3c by adhesive or the like.

Figure 3:
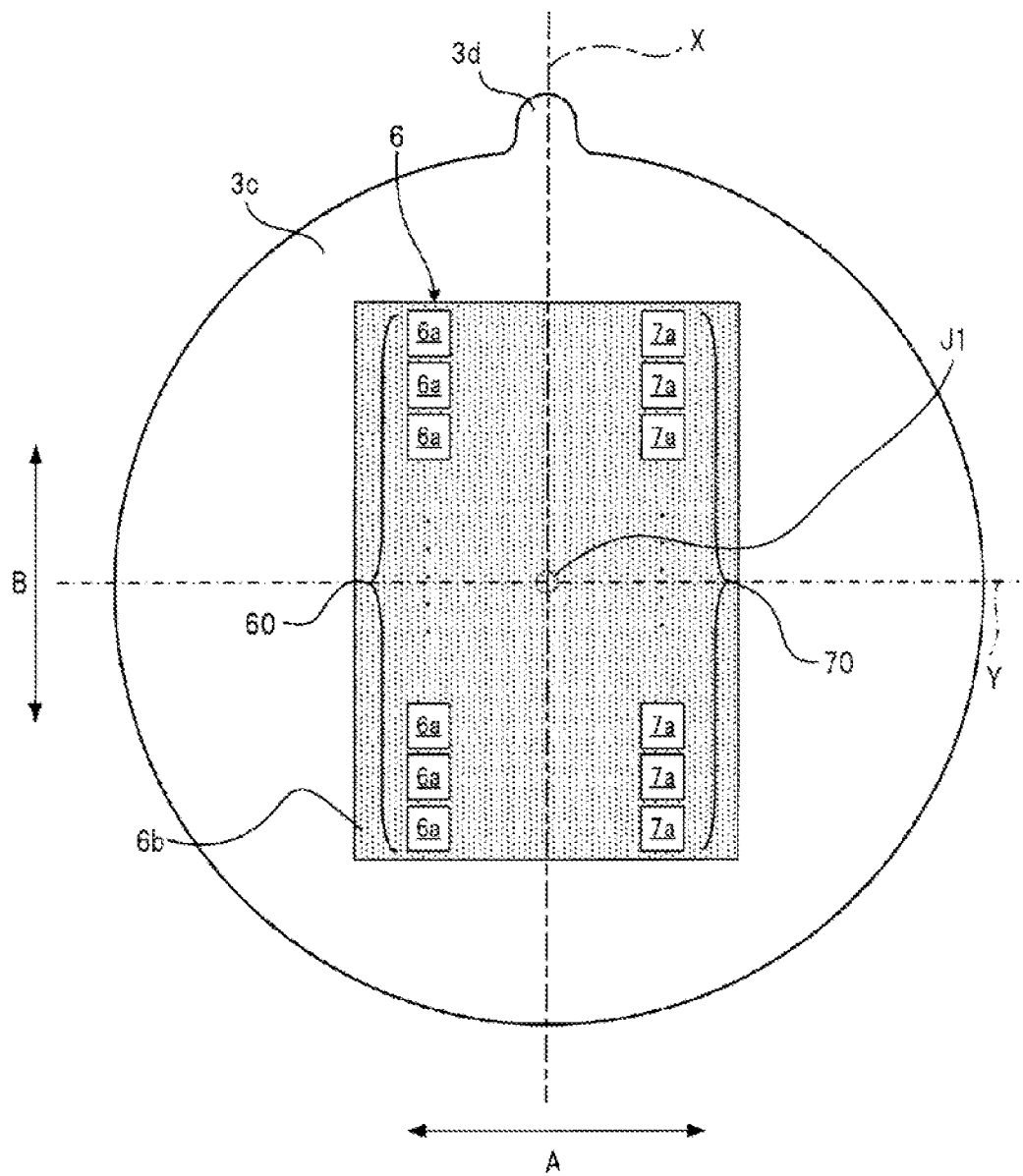
FIG. 3 is a plan view of a sensor table 3 and a sensor unit 6 of the pressure pulse wave measurement unit 100 shown in FIG. 1 as viewed in a direction opposite to a pressing direction.

FIG. 3 is a plan view of the sensor table 3 and the sensor unit 6 of the pressure pulse wave measurement unit 100 shown in FIG. 1 as viewed in a direction opposite to the pressing direction.

As shown in FIG. 3, element columns 60 and 70 are formed on the sensor surface 6b of the sensor unit 6 that is fixed to the sensor fixing surface 3c of the sensor table 3. The sensor surface 6b of the sensor unit 6 and the sensor fixing surface 3c are parallel to each other.

The element column 60 is constituted by a plurality of pressure detection elements 6a that are arranged side by side in a direction B (corresponding to one direction) that intersects (orthogonal, in the example in FIG. 3) a direction A in which the radial artery T, which exists in the attachment portion in the attachment state shown in FIG. 1, extends. The element column 70 is constituted by a plurality of pressure detection elements 7a that are arranged side by side in the direction B. The element columns 60 and 70 are arranged in the direction A. The sensor surface 6b of the sensor unit 6 has a rectangular shape that is long in the direction B, but is not limited thereto.

In the case where two directions or two axes are orthogonal to each other, in this specification, the angle (=90°) formed by these two directions or two axes may include a tolerance.

Each pressure detection element 6a and pressure detection element 7a that is located in the same position in the direction B as the pressure detection element 6a forms a pair. A plurality of the pairs are arranged in the direction B on the sensor surface 6b of the sensor unit 6.

The sensor surface 6b of the sensor unit 6 is a surface of a semiconductor substrate made of single crystal silicon or the like, and the pressure detection elements 6a and 7a are each constituted by a pressure sensitive diode or the like formed in the semiconductor substrate surface. The pressure detection element need only be an element that can be brought into contact with an object so as to detect a signal corresponding to the pressure, and is not specifically limited.

The pressure detection elements 6a (7a) are pressed toward the radial artery T such that the arrangement direction thereof intersects (is substantially orthogonal to) the radial artery T so as to detect a pressure oscillating wave, that is, a pressure pulse wave, that is generated from the radial artery T and is transmitted to the skin.

The intervals of the pressure detection elements 6a (7a) in the arrangement direction are sufficiently small such that a necessary and sufficient number of the pressure detection elements 6a (7a) are arranged above the radial artery T. The arrangement length of the pressure detection elements 6a (7a) is sufficiently large relative to the diameter dimension of the radial artery T.

The sensor table 3 is configured to be able to rotate about each of two axes that pass through a rotation axis J1 extending in the pressing direction and are orthogonal to the rotation axis J1.

A first axis X that passes through the rotation axis J1 and extends in a direction B and a second axis Y that passes through the rotation axis J1 and extends in the direction A are shown in FIG. 3. The sensor table 3 is supported by the fixed unit 4 such that the sensor fixing surface 3c is rotatable about each of the first axis X and the second axis Y.

In the example in FIG. 3, the position of the first axis X in the direction A is set to an arbitrary position between the element column 60 and the element column 70 (the middle in the example in FIG. 3). However, the position of the first axis X in the direction A is not limited thereto, and may be set on a left side of the element column 60, on a right side of the element column 70, or the like, for example.

Also, in the example in FIG. 3, the position of the second axis Y in the direction B is set on a line that equally divides each of the element column 60 and the element column 70. However, the position of the second axis Y in the direction B is not limited thereto, and may be set to any position on the element columns 60 and 70. Also, the position of the second axis Y in the direction B may be set to a position so as to not intersect the element columns 60 and 70 (upper or lower side of the element columns).

The direction connecting the rotation axis J1 and a later-described first contact member 3d provided in the sensor table 3 matches the direction B, which is a direction in which pressure detection elements included in each of the element column 60 and the element column 70 are arranged side by side. In this specification, the angle (=0°) formed by two directions when the two directions match may include a tolerance.

Figure 4:
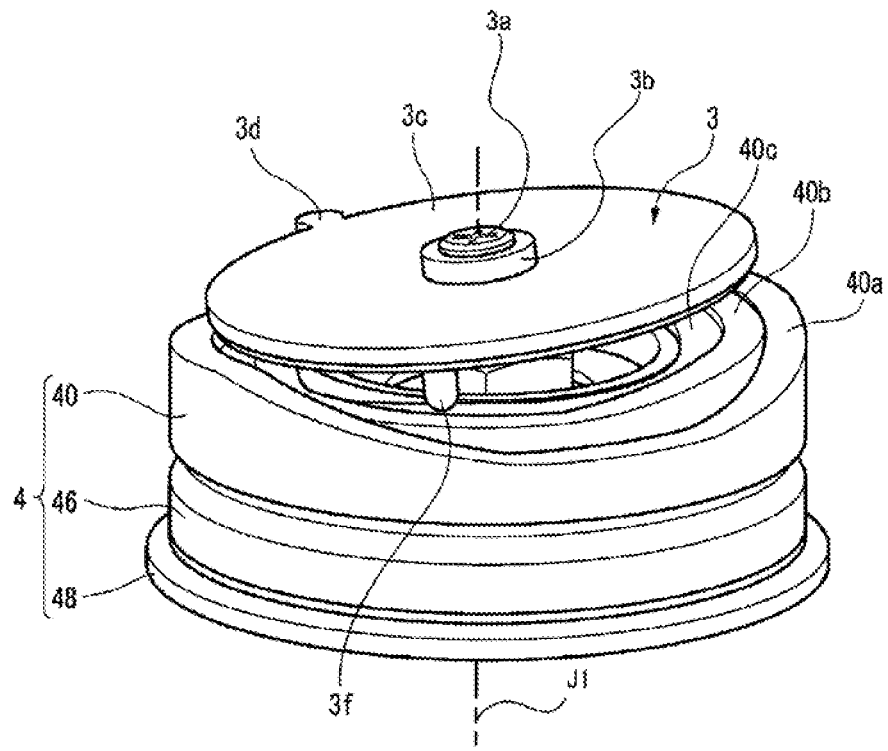
FIG. 4 is a perspective view schematically illustrating a detailed configuration of a rotation control member 5 in the pressure pulse wave measurement unit 100 shown in FIG. 2.
Figure 5:
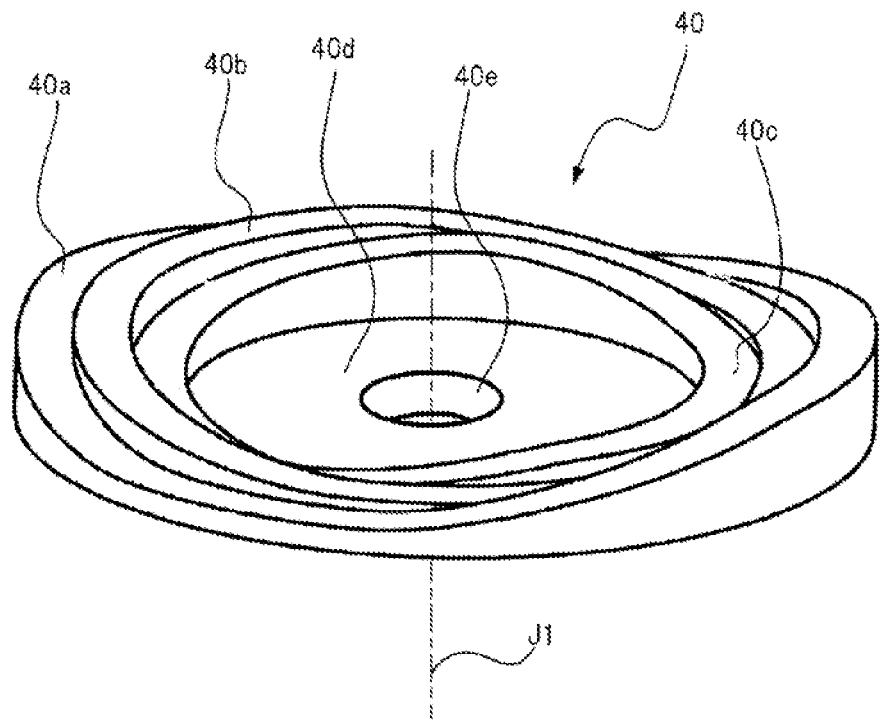
FIG. 5 is a perspective view schematically illustrating a ring cam 40 shown in FIG. 4.
Figure 6:
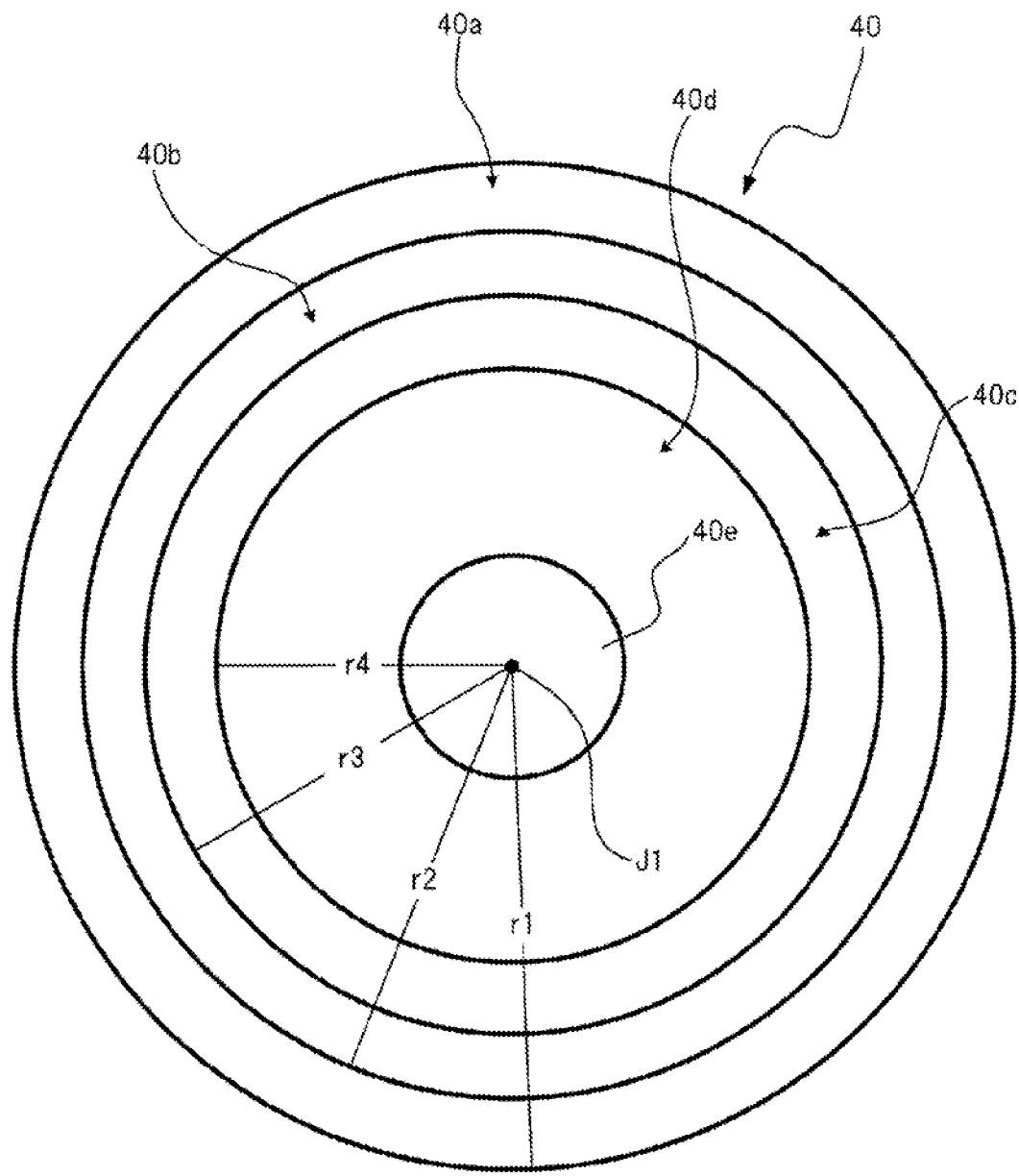
FIG. 6 is a plan view of the ring cam 40 shown in FIG. 5 as viewed in a direction opposite to a pressing direction.
Figure 7:
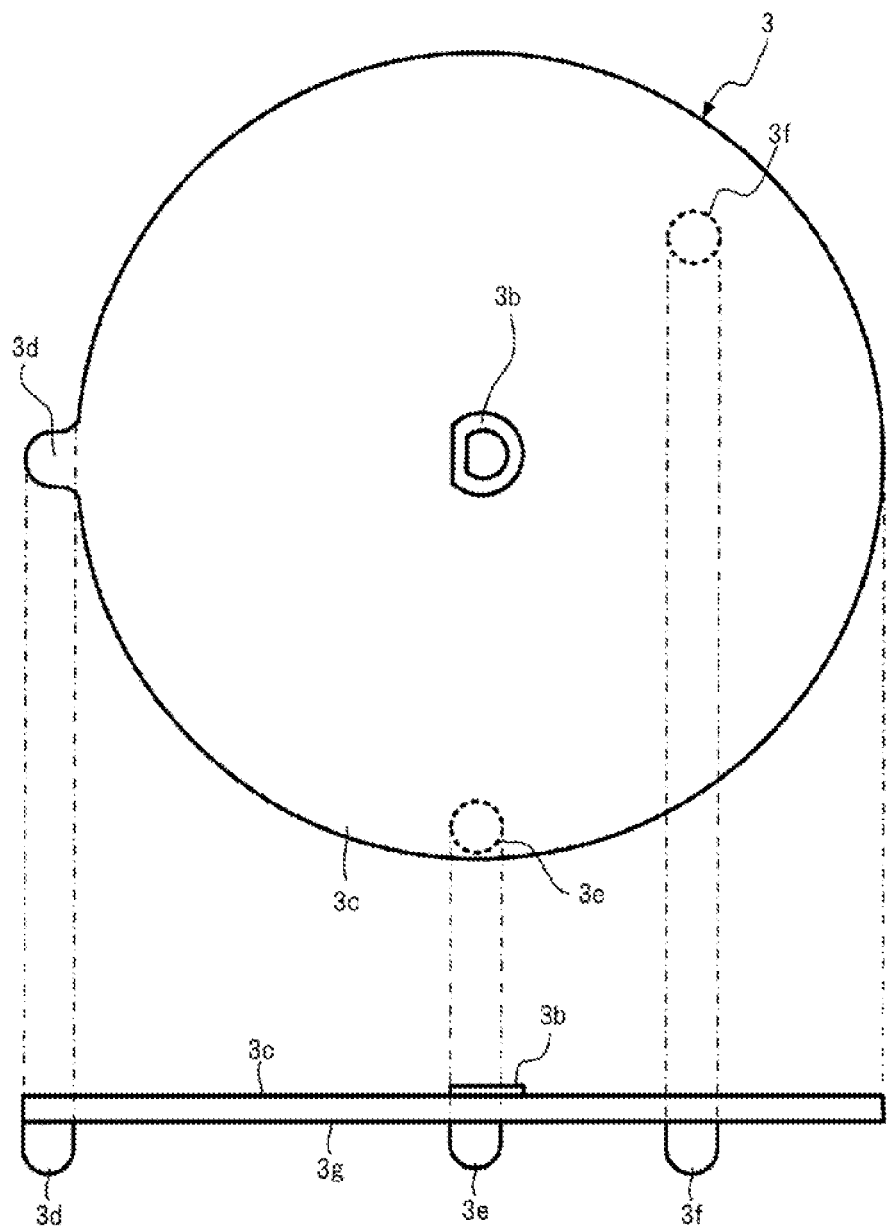
FIG. 7 is a diagram illustrating a plan view of the sensor table 3 shown in FIG. 4 as viewed in a direction perpendicular to a sensor fixing surface 3c, and a side view thereof as viewed in a direction parallel to the sensor fixing surface 3c.

FIG. 4 is a perspective view schematically illustrating a detailed configuration of the rotation control member 5 in the pressure pulse wave measurement unit 100 shown in FIG. 2. FIG. 5 is a perspective view schematically illustrating a ring cam 40 shown in FIG. 4. FIG. 6 is a plan view of the ring cam 40 shown in FIG. 5 as viewed in a direction opposite to the pressing direction. FIG. 7 is a diagram illustrating a plan view of the sensor table 3 shown in FIG. 4 as viewed in a direction perpendicular to the sensor fixing surface 3c, and a side view thereof as viewed in a direction parallel to the sensor fixing surface 3c.

The fixed unit 4 of the rotation control member 5 includes the ring cam 40 serving as a second member configured to be able to rotate about the rotation axis J11, an ultrasonic motor 46 for driving the ring cam 40 so as to rotate, and a base 48 that supports the sensor table 3 such that the sensor fixing surface 3c can rotate about each of the two axes (first axis X and second axis Y in FIG. 3) that are orthogonal to the pressing direction, a portion of the ultrasonic motor 46 being fixed to the base 48. The sensor table 3 is fixed to the base 48 by a fixing screw 3a.

As shown in FIGS. 5 and 6, the ring cam 40 has a thickness in the pressing direction, and is a substantially ring-shaped member in plan view in the pressing direction. One end surface (end surface on a side opposing the sensor table 3) of the ring cam 40 in the pressing direction is constituted by a first cam face 40a, a second cam face 40b, a third cam face 40c, and a bottom face 40d.

The first cam face 40a, the second cam face 40b, and the third cam face 40c are each formed so as to extend along a circumference of a circle centered about the rotation axis J1 of the ring cam 40.

The first cam face 40a, the second cam face 40b, and the third cam face 40c are each a face in which a predetermined rising and falling pattern is provided along a circumferential direction of a circle centered about the rotation axis J1. The rising and falling patterns will be described later.

As shown in FIG. 6, the first cam face 40a is constituted by a region that is surrounded by a circle of a radius r1 centered about the rotation axis J1 and a circle of a radius r2 (<r1) centered about the rotation axis J1.

The second cam face 40b is constituted by a region that is surrounded by a circle of a radius r2 centered about the rotation axis J1 and a circle of a radius r3 (<r2) centered about the rotation axis J1.

The third cam face 40c s constituted by a region that is surrounded by a circle of a radius r3 centered about the rotation axis J1 and a circle of a radius r4 (<r3) centered about the rotation axis J1.

A through hole 40e that reaches the other end surface in the pressing direction of the ring cam 40 for connecting the sensor table 3 and the base 48 is provided in the bottom face 40d of the ring cam 40.

As shown in FIGS. 4 and 7, a screw-fastening portion 3b for fixing the sensor table 3 to the base 48 is formed at a center portion of the sensor fixing surface 3c to which the sensor unit 6 of the sensor table 3 is fixed.

Also, a first contact member 3d that comes into contact with the first cam face 40a of the ring cam 40, a second contact member 3e that comes into contact with the second cam face 40b of the ring cam 40, and a third contact member 3f that comes into contact with the third cam face 40c of the ring cam 40 are formed on a back surface 3g of the sensor fixing surface 3c of the sensor table 3.

The first contact member 3d, the second contact member 3e, and the third contact member 3f are provided with rotatable spherical bodies at respective leading edges. As a result of the spherical bodies rotating, even if the ring cam 40 rotates, only the sensor fixing surface 3c inclines while the positions of the first contact member 3d, the second contact member 3e, and the third contact member 3f as viewed in the pressing direction are fixed.

Figure 8:
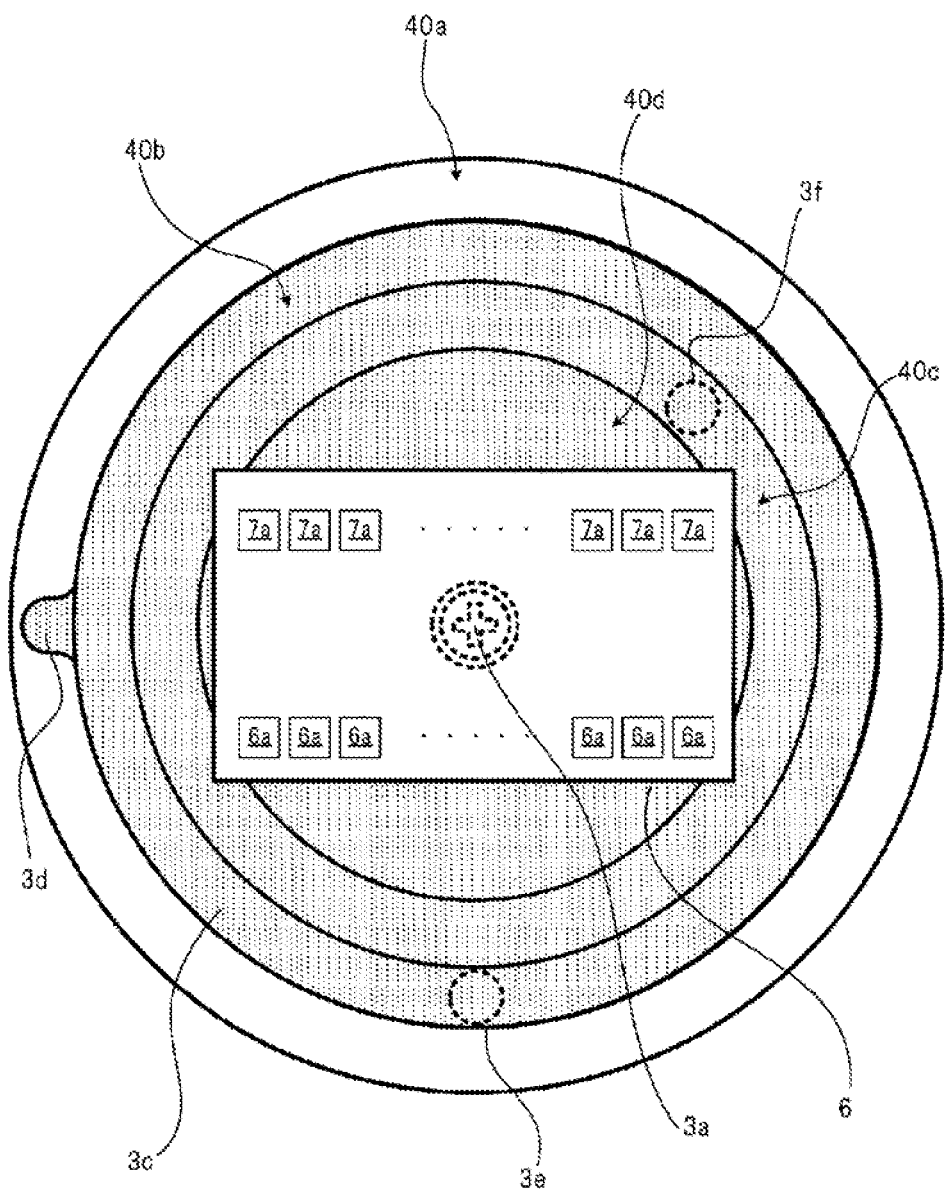
FIG. 8 is a plan view of the pressure pulse wave measurement unit 100, in a state in which the sensor fixing surface 3c of the sensor table 3 is perpendicular to the pressing direction, as viewed in a direction opposite to a pressing direction.

FIG. 8 is a plan view of the pressure pulse wave measurement unit 100, in a state in which the sensor fixing surface 3c of the sensor table 3 is perpendicular to the pressing direction, as viewed in a direction opposite to the pressing direction. Note that the illustration of the base 48, the air bladder 2, and the casing 1 are omitted in FIG. 8.

As shown in FIG. 8, the first contact member 3d is in contact with the first cam face 40a, the second contact member 3e is in contact with the second cam face 40b, and the third contact member 3f is in contact with the third cam face 40c.

In FIG. 8, a first contact point between the first contact member 3d and the first cam face 40a, a second contact point between the second contact member 3e and the second cam face 40b, and a third contact point between the third contact member 3f and the third cam face 40c are each on a surface that is perpendicular to the pressing direction.

Also, the sensor table 3 is designed such that only the first contact member 3d overlaps the first cam face 40a in FIG. 8.

When the ring cam 40 rotates about the rotation axis J1 in a state shown in FIG. 8, the heights of the above-described three contact points change with reference to a reference position, the reference position being a position of the end surface on a side opposing the base 48 of the ring cam 40 in the pressing direction. As a result of the changes in height of these three contact points, the sensor fixing surface 3c of the sensor table 3 rotates about the first axis X and the second axis Y.

In this way, a motion conversion mechanism that converts the rotational motion of the ring cam 40 to the rotational motion of the sensor unit 6 that is fixed to the sensor fixing surface 3c of the sensor table 3 about the first axis X and the second axis Y is constituted by the first cam face 40a, the second cam face 40b, the third cam face 40c, the first contact member 3d, the second contact member 3e, and the third contact member 3f.

The rising and falling pattern of the first cam face 40a is a pattern designed such that the sensor fixing surface 3c rotates about the first axis X as a result of the first contact member 3d moving relative to the first cam face 40a due to the rotational motion of the ring cam 40.

The rising and falling pattern of the second cam face 40b is a pattern designed such that the sensor fixing surface 3c rotates about the second axis Y as a result of the second contact member 3e moving relative to the second cam face 40b due to the rotational motion of the ring cam 40.

Note that the third contact member 3f of the sensor table 3 is provided for the purpose of stabilizing the orientation of the sensor table 3. Therefore, the rising and falling pattern of the third cam face 40c is designed such that the movement of the sensor fixing surface 3c about the first axis X at a desired rotational angle and the movement of the sensor fixing surface 3c about the second axis Y at a desired rotational angle are not disturbed.

Figure 9:
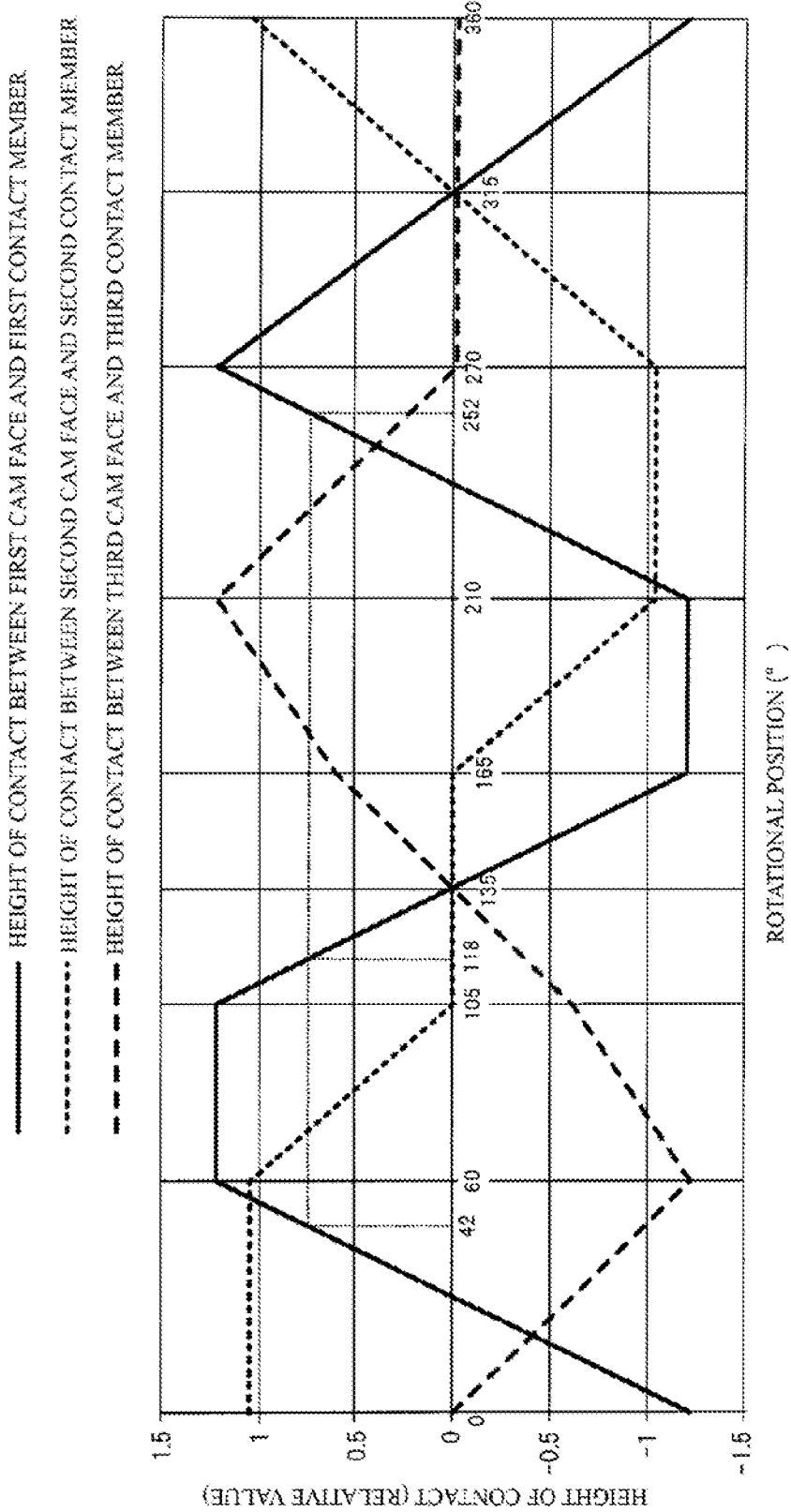
FIG. 9 is a diagram illustrating an example of the rising and falling patterns of a first cam face 40a, a second cam face 40b, and a third cam face 40c, respectively.

FIG. 9 is a diagram illustrating an example of the rising and falling patterns of the first cam face 40a, the second cam face 40b, and the third cam face 40c, respectively.

The vertical axis shown in FIG. 9 shows the heights of the above-described three contact points from a reference position, the reference position being a position of the end surface of the ring cam 40 on the base 48 side in the pressing direction. The heights on the vertical axis are shown as relative values relative to a reference value, the reference value (="0") being the height when the three contact points are at the same height in the state shown in FIG. 8.

The horizontal axis in FIG. 9 shows the rotational position of the ring cam 40 as an angle from 0° to 360°. In the example in FIG. 9, the heights of the contact points between the cam faces of the ring cam 40 and the contact members are at the reference value when the rotational position of the ring cam 40 is 135°.

As shown in FIG. 9, the height of the first contact point between the first cam face 40a and the first contact member 3d changes from a minimum value to a maximum value in a first range in which the rotational position is from 0° to 60°, and is fixed to the maximum value in a second range in which the rotational position is from 60° to 105°.

Also, the height of the first contact point changes from the maximum value to the minimum value in a third range in which the rotational position is from 105° to 165°, and is fixed to the minimum value in a fourth range in which the rotational position is from 165° to 210°.

Furthermore, the height of the first contact point changes from the minimum value to the maximum value in a fifth range in which the rotational position is from 210° to 270°, and changes from the maximum value to the minimum value in a sixth range in which the rotational position is from 270° to 360°.

The height of the second contact point between the second cam face 40b and the second contact member 3e is fixed to a maximum value in the first range (from 0° to 60°) of the rotational position, and changes from the maximum value to "0" in the second range (from 60° to 105°) of the rotational position.

Also, the height of the second contact point is fixed to "0" in the third range (from 105° to 165°) of the rotational position, and changes from "0" to a minimum value in the fourth range (from 165° to 210°) of the rotational position.

Furthermore, the height of the second contact point is fixed to the minimum value in the fifth range (from 210° to 270°) of the rotational position, and changes from the minimum value to the maximum value in the sixth range (from 270° to 360°) of the rotational position.

Note that, in actuality, each cam face inclines such that the change in height is smooth in the vicinity of each inflection point of the height of the contact point.

The first cam face 40a is designed such that the rotation angle of the sensor fixing surface 3c about the first axis X changes from −5° to +5° when the rotational position of the ring cam 40 changes from 0° to 60°.

The first cam face 40a is designed such that the rotation angle of the sensor fixing surface 3c about the first axis X is fixed at +5° when the rotational position of the ring cam 40 changes in a range from 60° to 105°.

The first cam face 40a is designed such that the rotation angle of the sensor fixing surface 3c about the first axis X changes from +5° to −5° when the rotational position of the ring cam 40 changes from 105° to 165°.

The first cam face 40a is designed such that the rotation angle of the sensor fixing surface 3c about the first axis X is fixed at −5° when the rotational position of the ring cam 40 changes in a range from 165° to 210°.

The first cam face 40a is designed such that the rotation angle of the sensor fixing surface 3c about the first axis X changes from −5° to +5° when the rotational position of the ring cam 40 changes from 210° to 270°.

The second cam face 40b is designed such that the rotation angle of the sensor fixing surface 3c about the second axis Y is fixed at +5° when the rotational position of the ring cam 40 changes in a range from 0° to 60°.

The second cam face 40b is designed such that the rotation angle of the sensor fixing surface 3c about the second axis Y changes from +5° to 0° when the rotational position of the ring cam 40 changes in a range from 60° to 105°.

The second cam face 40b is designed such that the rotation angle of the sensor fixing surface 3c about the second axis Y is fixed at 0° when the rotational position of the ring cam 40 changes in a range from 105° to 165°.

The second cam face 40b is designed such that the rotation angle of the sensor fixing surface 3c about the second axis Y changes from 0° to −5° when the rotational position of the ring cam 40 changes in a range from 165° to 210°.

The second cam face 40b is designed such that the rotation angle of the sensor fixing surface 3c about the second axis Y is fixed at −5° when the rotational position of the ring cam 40 changes in a range from 210° to 270°.

It is assumed that the rotation angle of the sensor fixing surface 3c about the first axis X is "0°" when the sensor fixing surface 3c is perpendicular to the pressing direction, increases as the sensor fixing surface 3c rotates, from this state, about the first axis X in one direction, and decreases as the sensor fixing surface 3c rotates in the other direction. In FIG. 9, if the height of the first contact point is the same, the rotation angle of the sensor fixing surface 3c about the first axis X is the same, regardless of the rotational position.

Also, it is assumed that the rotation angle of the sensor fixing surface 3c about the second axis Y is "0" when the sensor fixing surface 3c is perpendicular to the pressing direction, increases as the sensor fixing surface 3c rotates, from this state, about the second axis Y in one direction, and decreases as the sensor fixing surface 3c rotates in the other direction. In FIG. 9, if the height of the second contact point is the same, the rotation angle of the sensor fixing surface 3c about the second axis Y is the same, regardless of the rotational position.

According to the rising and falling patterns shown in FIG. 9, as a result of the cam faces moving relative to the respective contact members when the ring cam 40 rotates in the first range (from 0 to 60°), the rotation angle of the sensor fixing surface 3c about the first axis X changes in a range from +5° to −5°, while the rotation angle of the sensor fixing surface 3c about the second axis Y is fixed at +5°.

Also, as a result of the cam faces moving relative to the respective contact members when the ring cam 40 rotates in the third range (from 105° to 165°), the rotation angle of the sensor fixing surface 3c about the first axis X changes in a range from +5° to −5°, while the rotation angle of the sensor fixing surface 3c about the second axis Y is fixed at 0°.

Also, as a result of the cam faces moving relative to the respective contact members when the ring cam 40 rotates in the fifth range (from 210° to 270°), the rotation angle of the sensor fixing surface 3c about the first axis X changes in a range from +5° to −5°, while the rotation angle of the sensor fixing surface 3c about the second axis Y is fixed at −−5°.

In this way, the rotation control member 5 changes the rotation angle of the sensor unit 6 fixed to the sensor fixing surface 3c about the first axis X from end to end of the range of angles (from +5° to −5°) by which the sensor unit 6 fixed to the sensor fixing surface 3c can rotate about the first axis X, in respective states in which the rotation angle of the sensor unit 6 fixed to the sensor fixing surface 3c about the second axis Y is fixed to each of plurality of values (the three values −5°, 0°, and +5°, in the example in FIG. 9). Accordingly, the sensor unit 6 can be two-dimensionally rotated by amounts corresponding to the combinations of the three rotation angles about the second axis Y and all the available values of the rotation angle about the first axis X.

Note that, in the example in FIG. 9, in order to make the rotational position of the ring cam 40 return to the initial position when the ring cam 40 rotates 360° about the rotation axis J, the heights of the contact points differ even in the sixth range (from 270° to 360°). However, if the rotation position of the ring cam 40 is limited to the range from 0° to 270°, the heights of the contact points in the sixth range (from 270° to 360°) may take any pattern. The heights of the contact points in the sixth range (from 270° to 360°) may be the same as the respective heights at the rotational position 270, for example.

Also, it is also possible to design the inclinations of the cam faces such that, as a result of the ring cam 40 rotating 360° about the rotation axis J, combinations of three rotation angles (−5°, 0°, and +5°) about the second axis Y and all the available values (from −5° to +5°) of rotation angle about the first axis X can be realized.

Figure 10:
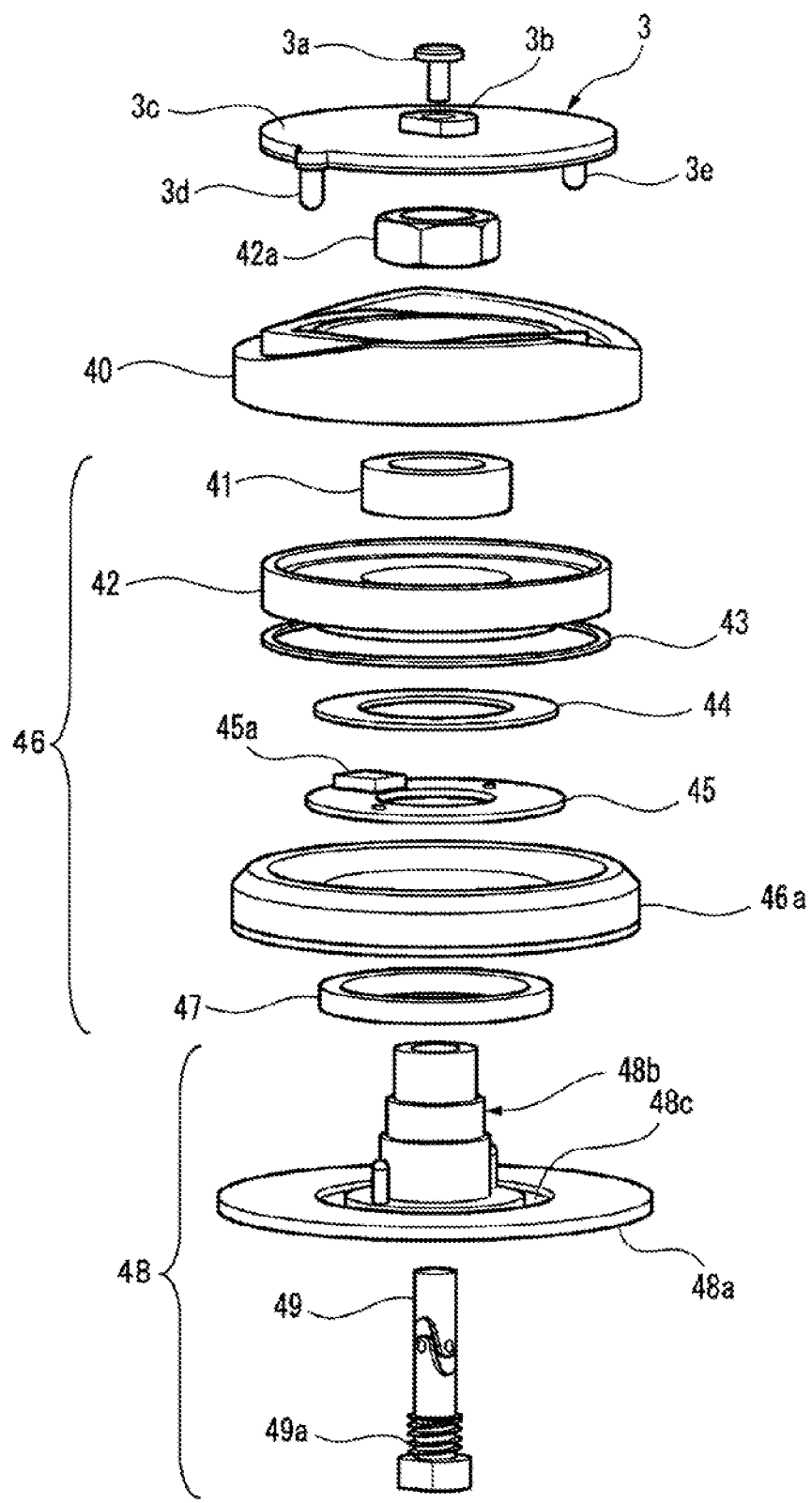
FIG. 10 is an exploded perspective view illustrating a detailed configuration of the rotation control member 5 shown in FIG. 4.

FIG. 10 is an exploded perspective view illustrating a detailed configuration of the rotation control member 5 shown in FIG. 4.

The base 48 shown in FIG. 4 includes a disk-shaped bottom portion 48a, a columnar shaft portion 48b that is provided in the bottom portion 48a and protrudes in the pressing direction, a universal joint 49 that is inserted into a hollow portion of the shaft portion 48b, and a spring 49a for pressing the sensor table 3.

A leading edge of the universal joint 49 is fixed to the sensor table 3 by a fixing screw 3a inserted into the screw-fastening portion 3b. The sensor table 3 is pressed by the spring 49a. A straight line that passes through the center of the shaft portion 48b and extends in the pressing direction constitutes the rotation axis J1.

The ultrasonic motor 46 shown in FIG. 4 includes a ring-shaped rotor 42 into which the shaft portion 48b of the base 48 is inserted, a bearing member 41 provided between a hollow portion of the rotor 42 and the shaft portion 48b, a ring-shaped stator 46a that accommodates the rotor 42 and causes the rotor 42 to rotate, a slide plate 43 fixed to the rotor 42, a slit plate 44 that is fixed to the rotor 42 and in which a slit is formed, an encoder plate 45 that is fixed to the bottom portion 48a of the base 48 and in which an encoder 45a that detects the slit of the slit plate 44 so as to detect the rotational position of the rotor 42 is formed, and a pressing spring 47 that is housed in a recess 48c provided in the bottom portion 48a of the base 48 and presses the stator 46a. The rotor is fixed to the ring cam 40 by a bolt 42a. The stator 46a is fixed to the bottom portion 48a of the base 48.

Figure 11:
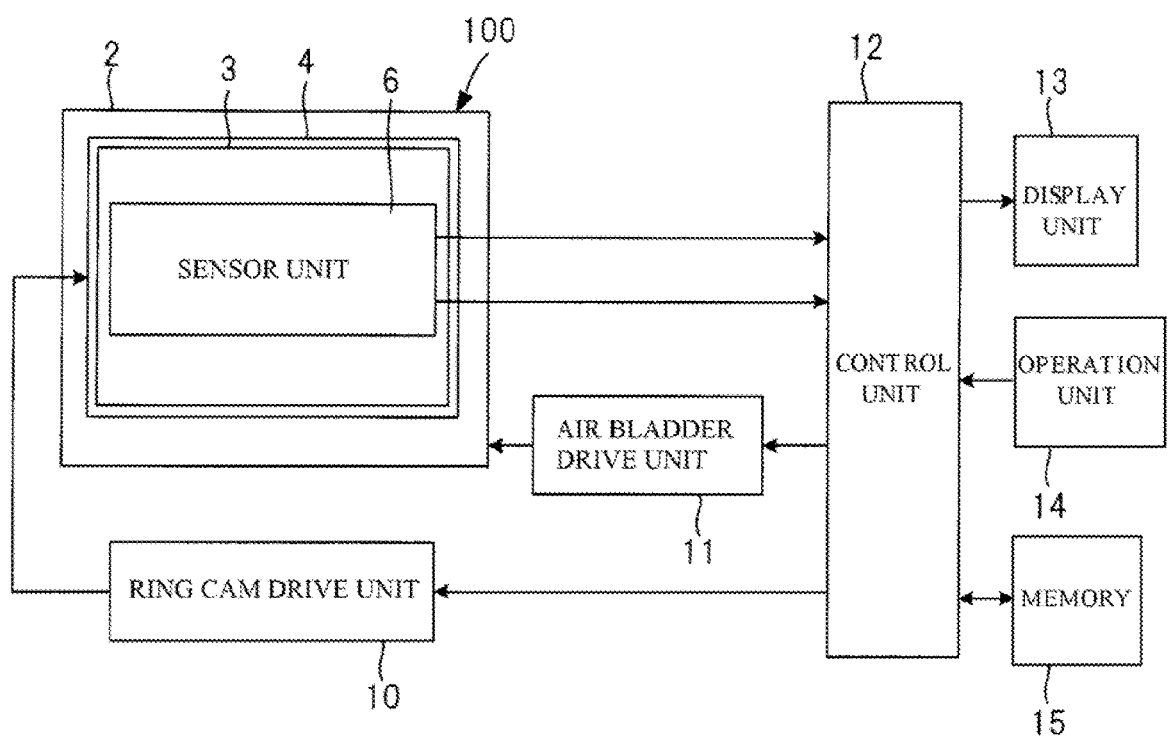
FIG. 11 is a schematic diagram illustrating a block configuration of a blood pressure measurement apparatus.

FIG. 11 is a schematic diagram illustrating a block configuration of a blood pressure measurement apparatus.

The blood pressure measurement apparatus includes the pressure pulse wave measurement unit 100, a ring cam drive unit 10, an air bladder drive unit 11, a control unit 12 that performs overall control on the apparatus, a display unit 13, an operation unit 14, and a memory 15.

The ring cam drive unit 10, under the instruction of the control unit 12, drives the stator 46a that constitutes the rotation control member 5 of the pressure pulse wave measurement unit 100 so as to rotate the ring cam 40 about the rotation axis J1.

The air bladder drive unit 11, under the instruction of the control unit 12, controls the amount of air (internal pressure of the air bladder 2) to be injected into the air bladder 2.

The display unit 13 is for displaying various types of information such as a measured blood pressure value, and is constituted by a liquid crystal display or the like, for example.

The operation unit 14 is an interface for inputting an instruction signal to the control unit 12, and is constituted by a button and the like for instructing a start of various types of operations including blood pressure measurement.

The memory 15 includes a ROM (Read Only Memory) for storing a program for causing the control unit 12 to perform a predetermined operation and data, a RAM (Random Access Memory) serving as a work memory, a flash memory for storing various types of information such as measured blood pressure data, and the like.

The control unit 12 functions as a bodily information calculation unit that calculates blood pressure information, as the bodily information, based on a pressure pulse wave detected by the pressure detection elements of the sensor unit 6. Here, the blood pressure information is taken as an example of the bodily information, but the bodily information may be any information as long as the information can be calculated based on the pressure pulse wave. For example, the pulse rate, the heart rate, and the like may be calculated as the bodily information, for example.

Hereinafter, operations of the blood pressure measurement apparatus of the present embodiment will be described. The blood pressure measurement apparatus of the present embodiment has a continuous blood pressure measurement mode in which blood pressure values (SBP (Systolic Blood pressure), which is a so-called maximum blood pressure, and DBP (Diastolic Blood pressure), which is a so-called minimum blood pressure) are measured for each pulse, and are displayed in the display unit 13.

Figure 12:
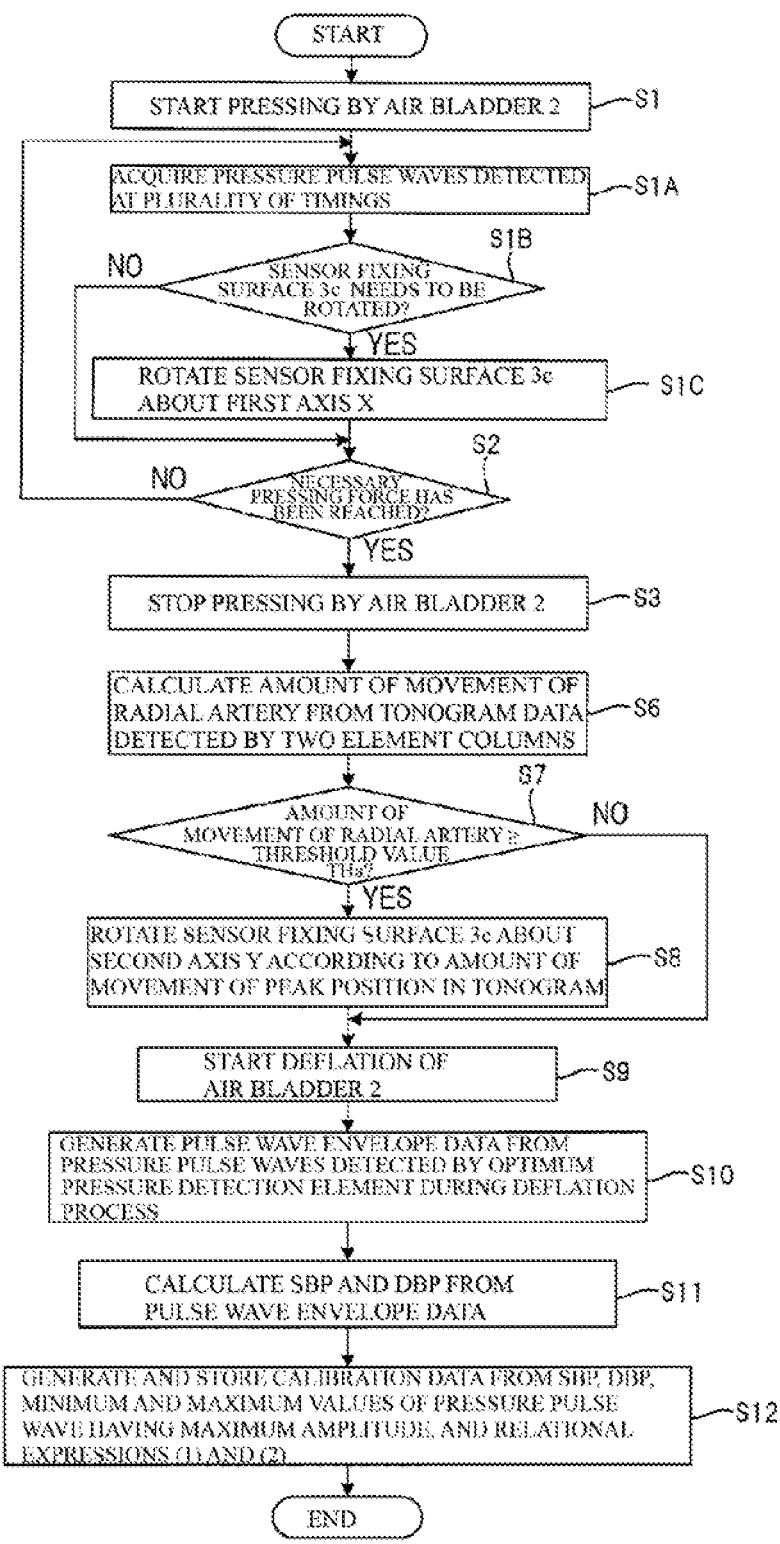
FIG. 12 is a flowchart for describing operations of the blood pressure measurement apparatus of the present embodiment up to when calibration data is generated in a continuous blood pressure measurement mode.

FIG. 12 is a flowchart for describing operations of the blood pressure measurement apparatus of the present embodiment up to when calibration data is generated in the continuous blood pressure measurement mode.

Note that it is assumed that, in an initial state of the sensor table 3 of the pressure pulse wave measurement unit 100 before an instruction to measure the blood pressure is given, the rotation angle about the first axis X and the rotation angle about the second axis Y are each 0°, and the sensor fixing surface 3c and the sensor surface 6b are perpendicular to the pressing direction.

When an instruction to measure the blood pressure is given, the control unit 12 controls the air bladder drive unit 11 so as to start injection of air to the air bladder 2, and increases the pressing force of the rotation control member 5 toward the radial artery T (step S1).

During the process of increasing the pressing force, at a certain timing (periodic timing, for example) after a sufficient time needed for blocking of the radial artery T being started has elapsed, out of pressure pulse waves (referred to as pressure pulse wave information I1) that have been detected by the pressure detection elements 6a and stored in the memory 15, the control unit 12 acquires the plurality of (two, in the following) pieces of pressure pulse wave information I1 with the most recent detection time instants. Also, at the certain timing, out of pressure pulse waves (referred to as pressure pulse wave information I2) that have been detected by the pressure detection elements 7a and stored in the memory 15, the control unit 12 acquires the plurality of (two, in the following) pieces of pressure pulse wave information I2 with the most recent detection time instants (step S1A).

The control unit 12 calculates an average value Ave1 of the amplitude, for example, of the pressure pulse wave that constitutes the pressure pulse wave information I1 detected at time instant t1 out of the two pieces of pressure pulse wave information I1 acquired in step S1A, and calculates an average value Ave2 of the amplitude of the pressure pulse wave that constitutes the pressure pulse wave information I1 detected at time instant t2 after the time instant t1. Also, the control unit 12 the calculates an average value Ave3 of the amplitude of the pressure pulse wave that constitutes the pressure pulse wave information I2 detected at time instant t1 out of the two pieces of pressure pulse wave information I2 acquired in step S1A, and calculates an average value Ave4 of the amplitude of the pressure pulse wave that constitutes the pressure pulse wave information I2 detected at time instant t2. Also, the control unit 12 calculates ratios ((Ave1/Ave3) and (Ave2/Ave4)) of the average values calculated with respect to the same time instant.

Next, the control unit 12 determines whether or not the sensor fixing surface 3c should be rotated about the first axis X based on the change in the ratio calculated with respect to the plurality of timings. That is, the control unit 12 determines whether or not the sensor fixing surface 3c should be rotated about the first axis X based on the pressure pulse waves detected by the pressure detection elements 6a and 7a at a plurality of timings during a process of increasing the pressing force (step S1B).

For example, in the case where the ratios calculated with respect to the plurality of timings monotonically increase, it can be determined that, although the element column 70 is oriented in a direction of blocking the radial artery T, the element column 60 is not oriented in the direction of blocking the radial artery T. Therefore, the control unit 12 determines that the sensor fixing surface 3c needs to be rotated about the first axis X.

Also, in the case where the ratios calculated with respect to the plurality of timings monotonically decrease, it can be determined that although the element column 60 is oriented in the direction of blocking the radial artery T, the element column 70 is not oriented in the direction of blocking the radial artery T. Therefore, the control unit 12 determines that the sensor fixing surface 3c needs to be rotated about the first axis X.

Also, in the case where the ratios calculated with respect to the plurality of timings hardly change, it can be determined that the element columns 60 and 70 similarly detected the pressure pulse wave of the radial artery T. Therefore, the control unit 12 determines that the sensor fixing surface 3c need not be rotated about the first axis X.

Also, in the case where the ratios calculated with respect to the plurality of timings repeatedly increase and decrease, it cannot be determined whether the element columns 60 and 70 sufficiently press the radial artery T, or only one of the element columns does not sufficiently press the radial artery T. Therefore, the control unit 12 determines that the sensor fixing surface 3c need not be rotated about the first axis X.

In this way, the control unit 12 determines whether or not the sensor fixing surface 3c needs to be rotated about the first axis X based on the change in the ratios calculated with respect to a plurality of timings. Note that, instead of this ratio, a difference (value considering the sign) between the average value Ave1 (Ave2) and the average value Ave3 (Ave4) may be used. The method of determining whether or not the sensor fixing surface 3c needs to be rotated in this description is merely an example, and the method is not limited thereto.

Figure 13A:
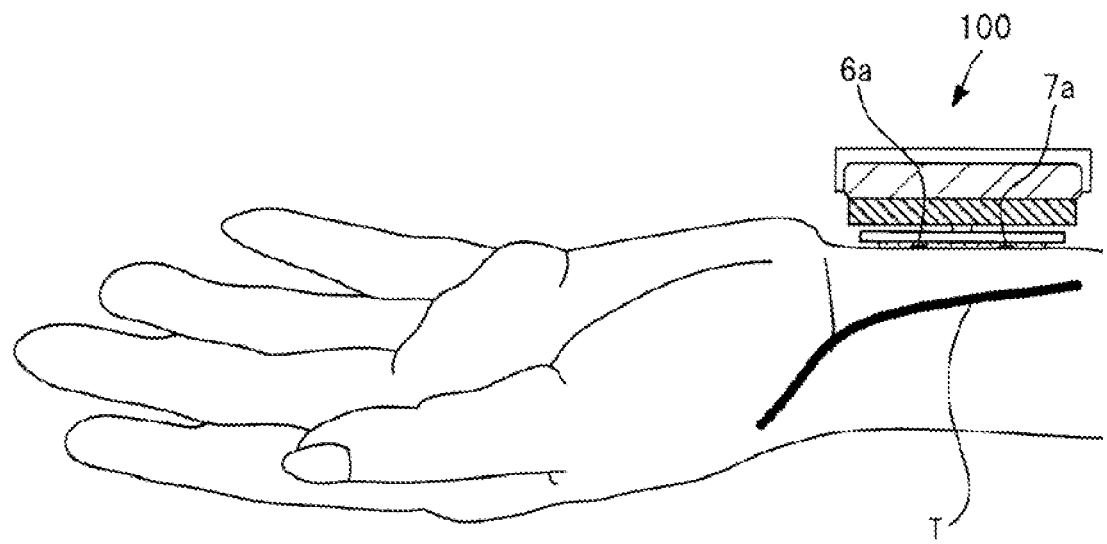
FIGS. 13A and 13B are diagram each of which illustrates an example of a state in which one of two element columns does not block the radial artery.

FIG. 13A is a diagram illustrating an example of a state in which, although the radial artery T is blocked by the element column 70, the radial artery T is not blocked by the element column 60. In the state of FIG. 13A, the distance between the element column 60 and the radial artery T is larger than the distance between the element column 70 and the radial artery T.

When the average value of the amplitude of a pressure pulse wave detected by each pressure detection element 6a is denoted as 6A, and the average value of the amplitude of a pressure pulse wave detected by each pressure detection element 7a is denoted as 7A, in the state of FIG. 13A, the ratio between 6A and 7A (6A/7A) is substantially larger than one. In this state, if the element column constituted by the pressure detection element 6a is brought closer to the radial artery T, the value (6A/7A) approaches one.

Therefore, upon determining that the sensor fixing surface 3c needs to be rotated about the first axis X in step S1B, the control unit 12 performs control so as to rotate the sensor fixing surface 3c about the first axis X according to the value (6A/7A) at the most recent time instant (step S1C).

Specifically, the control unit 12 refers to a data table (experimentally obtained and stored in the memory 15 before the product is shipped) indicating the relationship between the values (6A/7A) and the rotation angles of the sensor fixing surface 3c, reads out the rotation angle corresponding to the value (6A/7A), and sets the read-out rotation angle. The rotation angles of the sensor fixing surface 3c about the first axis X to be stored in the memory 15 are values between −5° to +5° inclusive (if the resolution is 1°, there are 11 in total, namely −5°, −4°, . . . , 0°, 1°, 2°, . . . , 5°). The resolution of the rotation angle is determined by a position detection resolution of the encoder 45a or the like.

Figure 13B:
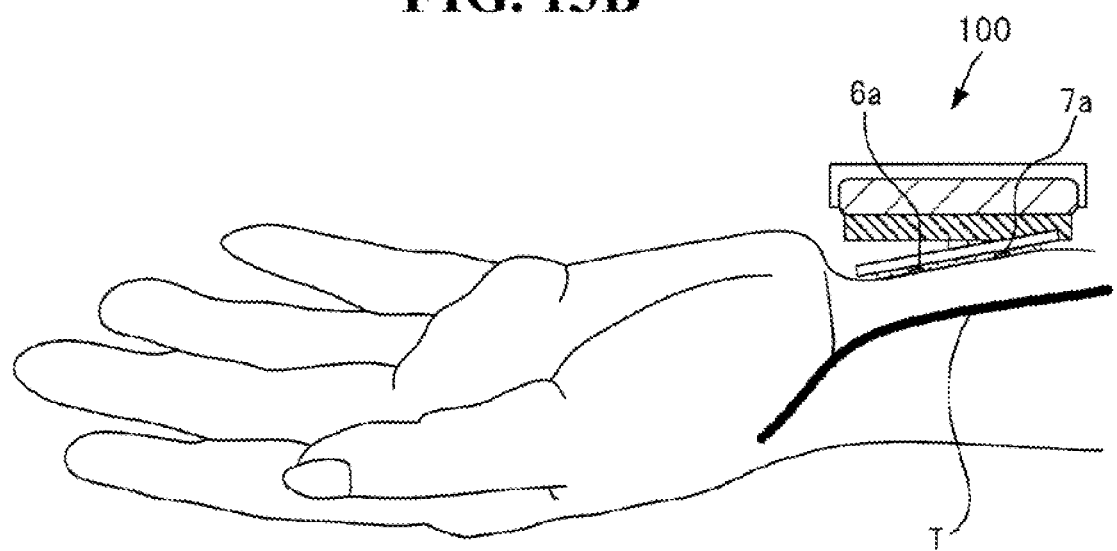

The control unit 12 rotates the sensor fixing surface 3c about the first axis X by a rotation angle that has been set in this way. Accordingly, as shown in FIG. 13B, the sensor fixing surface 3c can be made parallel to the radial artery T, and a state can be achieved in which each of the element columns 60 and 70 blocks the radial artery T.

The control unit 12 advances the processing to step S2 after step S1C and when it is determined in step S1C that the sensor fixing surface 3c need not be rotated about the first axis X. In step S2, the control unit 12 determines whether or not the pressing force has reached a force (necessary pressing force) that is sufficient to block the radial artery T. Upon determining that the pressing force has reached the necessary pressing force (step S2: YES), the control unit 12 controls the air bladder drive unit 11 so as to stop injection of air into the air bladder 2 (step S3). Upon determining that the pressing force has not reached the necessary pressing force, the control unit 12 returns the processing to step S1A.

After step S3, the control unit 12 obtains an amplitude distribution curve, which is a so-called tonogram, that indicates the relationship between the amplitudes of the respective pressure pulse waves detected by the pressure detection elements 6a at the same time instant, during steps S1 to S3, and the positions of the respective pressure detection elements 6a on the sensor surface 6b. Also, the control unit 12 obtains a tonogram that indicates the relationship between the amplitudes of the respective pressure pulse waves detected by the pressure detection element 7a at the same time instant and the positions of the respective pressure detection elements 7a on the sensor surface 6b.

The control unit 12 stores the tonogram that has been generated with respect to the element column 60, the identification information of the element column 60, the time instant at which the pressure pulse waves have been detected, and the pressing force (internal pressure of the air bladder 2) in the pressing direction by the air bladder 2 at this detection time instant in association with each other in the memory 15.

Similarly, the control unit 12 stores the tonogram that has been generated with respect to the element column 70, the identification information of the element column 70, the time instant at which the pressure pulse waves have been detected, and the pressing force in the pressing direction by the air bladder 2 at this detection time instant in association with each other in the memory 15.

Then, the control unit 12 uses the tonogram data stored in the memory 15 to calculate the amount of movement of the radial artery T in the direction B (direction that intersects the direction in which the radial artery T extends) while the rotation control member 5 presses the wrist (step S6).

Figure 14A:
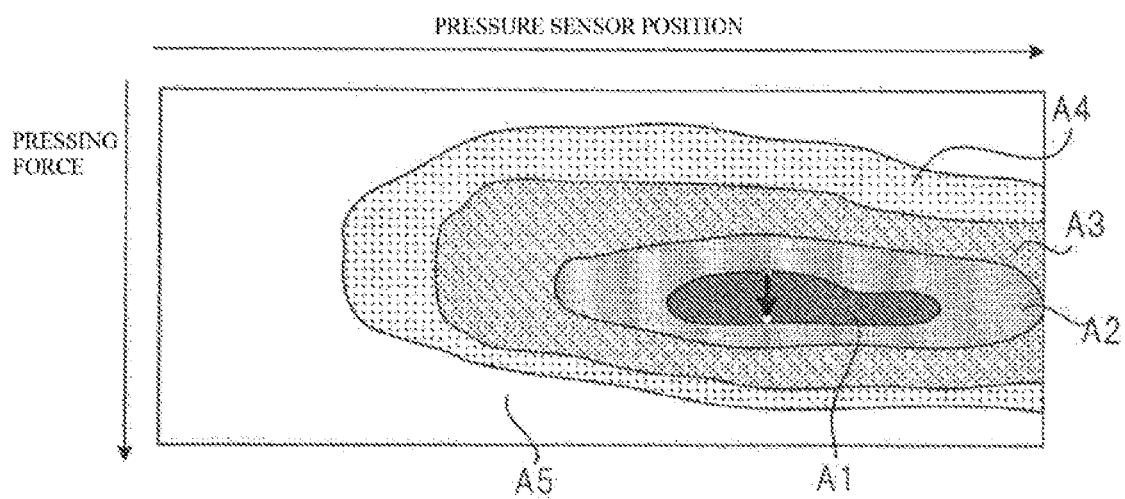
FIGS. 14A and 14B are diagrams each of which illustrates an example of amplitude values of pressure pulse waves detected by respective pressure detection elements in the sensor unit 6 when the pressing force applied by the sensor unit 6 to a wrist is changed.
Figure 14B:
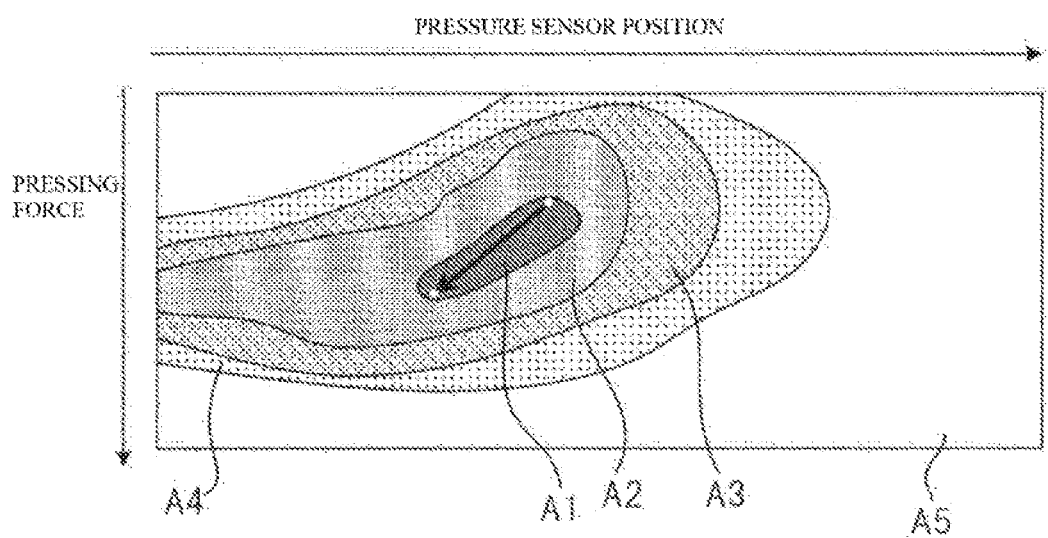

FIGS. 14A and 14B are diagrams illustrating examples of the amplitude values of the pressure pulse waves detected by the respective pressure detection elements 6a in the sensor unit 6 when the pressing force applied by the sensor unit 6 to a wrist is changed. In FIGS. 14A and 14B, the horizontal axis shows the position of each pressure detection element 6a in the direction B, and the vertical axis shows the pressing force.

In FIGS. 14A and 14B, the amplitudes of the pressure pulse waves detected by the pressure detection elements 6a at respective positions are color-coded according to the magnitude of the amplitude.

A reference sign A1 indicates a portion in which the amplitude is greater than or equal to a threshold value TH1. A reference sign A2 indicates a portion in which the amplitude is greater than or equal to a threshold value TH2 and less than the threshold value TH1. A reference sign A3 indicates a portion in which the amplitude is greater than or equal to a threshold value TH3 and less than the threshold value TH2. A reference sign A4 indicates a portion in which the amplitude is greater than or equal to a threshold value TH4 and less than the threshold value TH3. A reference sign A5 indicates a portion in which the amplitude is less than the threshold value TH4. Note that, threshold value TH1>threshold value TH2>threshold value TH3>threshold value TH4 is assumed.

FIG. 14A shows an example in which, during the process of increasing the pressing force, the positions of the pressure detection elements 6a that detect a pressure pulse wave having an amplitude that is greater than or equal to the threshold value TH1 are substantially the same. In contrast, FIG. 14B shows an example in which, during the process of increasing the pressing force, the positions of the pressure detection elements 6a that detect a pressure pulse wave having an amplitude that is greater than or equal to the threshold value TH1 shift to the left.

Figure 15A:
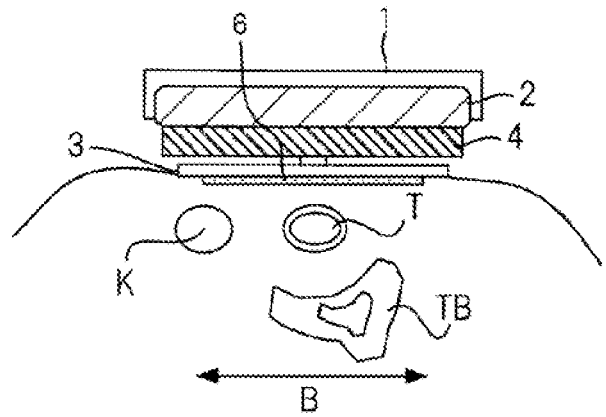
FIGS. 15A, 15B and 15C are diagrams each of which illustrates a state in which the pressure pulse wave measurement unit 100 is brought into contact with a wrist, and the sensor unit 6 is being pressed against the wrist by an air bladder 2.
Figure 15B:
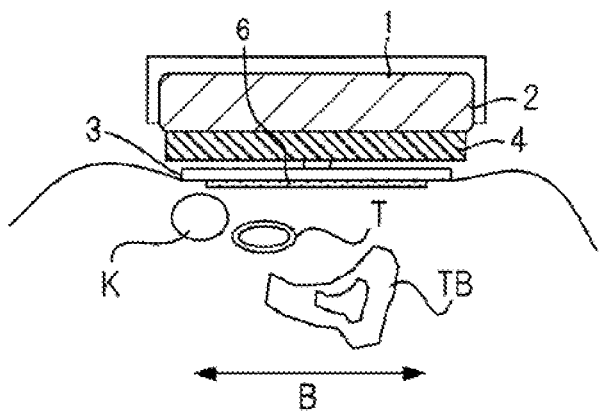
Figure 15C:
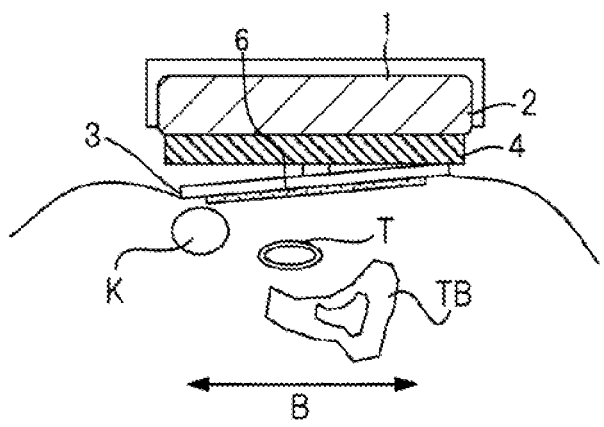

FIGS. 15A, 15B and 15C are diagrams each of which illustrates a state in which the pressure pulse wave measurement unit 100 is in contact with a wrist, and the sensor unit 6 is being pressed toward the wrist by the air bladder 2. In FIGS. 15A, 15B and 15C, the reference sign TB denotes the radial bone, and the reference sign K denotes a tendon.

When the sensor unit 6 is being pressed to the wrist from the state shown in FIG. 15A, it is possible that the radial artery T moves in the direction B as shown in FIG. 15B.

If the radial artery T moves in the direction B during pressing as shown in FIG. 15B, the distribution of the amplitude values of the pressure pulse waves during pressing is as shown in FIG. 14B. That is, there is a large shift between the position of the pressure detection element 6a that has detected a pressure pulse wave having an amplitude that is greater than or equal to the threshold value TH1, at the pressing force at which the amplitude is first detected, and the position of the pressure detection element 6a that has detected a pressure pulse wave having an amplitude that is greater than or equal to the threshold value TH1, at the pressing force at which the amplitude is finally detected.

In the example shown in FIG. 14A, there is not a substantial difference between the position of the pressure detection element 6a that has detected a pressure pulse wave having an amplitude that is greater than or equal to the threshold value TH1, at the pressing force at which the amplitude is first detected, and the position of the pressure detection element 6a that has detected a pressure pulse wave having an amplitude that is greater than or equal to the threshold value TH1, at the pressing force at which the amplitude is finally detected. That is, it can be understood that during the process of increasing the pressing force, the radial artery is blocked while not substantially being moved in the direction B.

In this way, as a result of checking the change in the tonogram during the process of changing the pressing force, the change in the position of the radial artery T in the direction B can be detected. It is possible that if the radial artery T is blocked while increasing the pressing force in a state shown in FIG. 15B, an accurate tonogram cannot be acquired due to the influence of biological tissue such as the tendon K.

Therefore, in step S6, based on the data in FIGS. 14A and 14B showing the relationship between the pressing force and the tonogram, the control unit 12 calculates the difference between (that is, the amount of movement of the radial artery T in the direction B) the position of the pressure detection element 6a that has detected a pressure pulse wave having an amplitude that is greater than or equal to the threshold value TH1, at the pressing force at which the amplitude is first detected, and the position of the pressure detection element 6a that has detected a pressure pulse wave having an amplitude that is greater than or equal to the threshold value TH1, at the pressing force at which the amplitude is finally detected, and the control unit 12 determines whether or not the calculated difference is greater than or equal to a threshold value THa (step S7).

If the difference between two positions is greater than or equal to the threshold value THa (step S7: YES), the control unit 12 obtains, in step S8, a vector indicated by the arrow in FIG. 14B. If the difference between two positions is less than the threshold value THa (step S7: NO), the processing in step S9 is performed.

The direction and size of the vector shown in FIGS. 14A and 14B and information regarding the rotation angle of the sensor fixing surface 3c about the second axis Y are experimentally obtained and associated with each other in advance, and the result is stored in the memory 15. The rotation angle of the sensor fixing surface 3c about the second axis Y to be stored in the memory 15 takes three values, namely −5°, 0°, and +5°.

Then, the control unit 12 acquires the information regarding the rotation angle corresponding to the size and direction of the obtained vector from the memory 15, and transmits the acquired information to the ring cam drive unit 10. Then, the ring cam drive unit 10 rotates the ring cam 40 such that the rotation angle of the sensor fixing surface 3c about the second axis Y becomes a desired value, while maintaining the rotation angle of the sensor fixing surface 3c about the first axis X, based on the received information and the rotation angle of the sensor fixing surface 3c about the first axis X set in step S1C. Accordingly, the sensor fixing surface 3c is rotated as shown in FIG. 15C (step S8).

For example, consider a case where, as a result of the processing in step S1C, the rotational position of the ring cam 40 is controlled to 118° (the rotation angle about the first axis X is assumed to be +3°). Also, it is assumed that the rotation angle about the second axis Y needs to be +5° in step S8. In this case, in step S8, as a result of the rotational position of the ring cam 40 being changed to 42°, the rotation angle about the second axis Y becomes +5° while the rotation angle about the first axis X is kept at +3°. Also, in the case where, in step S8, the rotation angle about the second axis Y needs to be −5°, as a result of the rotational position of the ring cam 40 being changed to 252°, the rotation angle about the second axis Y becomes −5° while the rotation angle about the first axis X is kept at +3°.

As described above, when the blood pressure measurement is instructed, control unit 12 determines, in steps S1B and S7, whether or not the sensor fixing surface 3c needs to be rotated, based on the pressure pulse waves detected by the pressure detection elements 6a and 7a at a plurality of timings during the process of increasing the pressing force by the air bladder 2. Then, if the sensor fixing surface 3c needs to be rotated (step S1B: YES, step S7: YES), the control unit 12 rotates the sensor fixing surface 3c based on the pressure pulse waves detected by the pressure detection elements 6a and 7a.

In step S9 subsequent to step S8, the control unit 12 controls the air bladder drive unit 11 so as to discharge the air inside the air bladder 2 and start decreasing the pressing force on the radial artery T.

After starting the decrease of the pressing force in step S9 and reducing the pressing force to a minimum value, the control unit 12 determines an optimum pressure detection element among the pressure detection elements 6a and 7a. The control unit 12 determines the pressure detection element that has detected a pressure pulse wave having a maximum amplitude during the process of decreasing the pressing force as the optimum pressure detection element, for example.

The pressure pulse wave detected by the pressure detection element that is located immediately above a flat portion of the radial artery T is not influenced by the tension of a wall of the radial artery T, and has the maximum amplitude. Also, this pressure pulse wave has the maximum correlation with the blood pressure value inside the radial artery T. According to these reasons, the pressure detection element that has detected the pressure pulse wave having the maximum amplitude is determined as the optimum pressure detection element.

Note that in the case where there are a plurality of pressure detection elements that have detected a pressure pulse wave having the maximum amplitude, these plurality of pressure detection elements may be treated as the optimum pressure detection element, and the average of the pressure pulse waves detected by the plurality of pressure detection elements may be treated as the pressure pulse wave detected by the optimum pressure detection element, for example.

Then, the control unit 12 generates pulse wave envelope data from pressure pulse waves detected by the optimum pressure detection element during the process of decreasing the pressing force (step S10).

The pulse wave envelope data is data in which a pressing force by the sensor unit 6 to the radial artery T (internal pressure of the air bladder 2) is associated with the amplitude of a pressure pulse wave detected by the optimum pressure detection element in a state in which the optimum pressure detection element is pressed toward the radial artery T with this pressing force.

Figure 16:
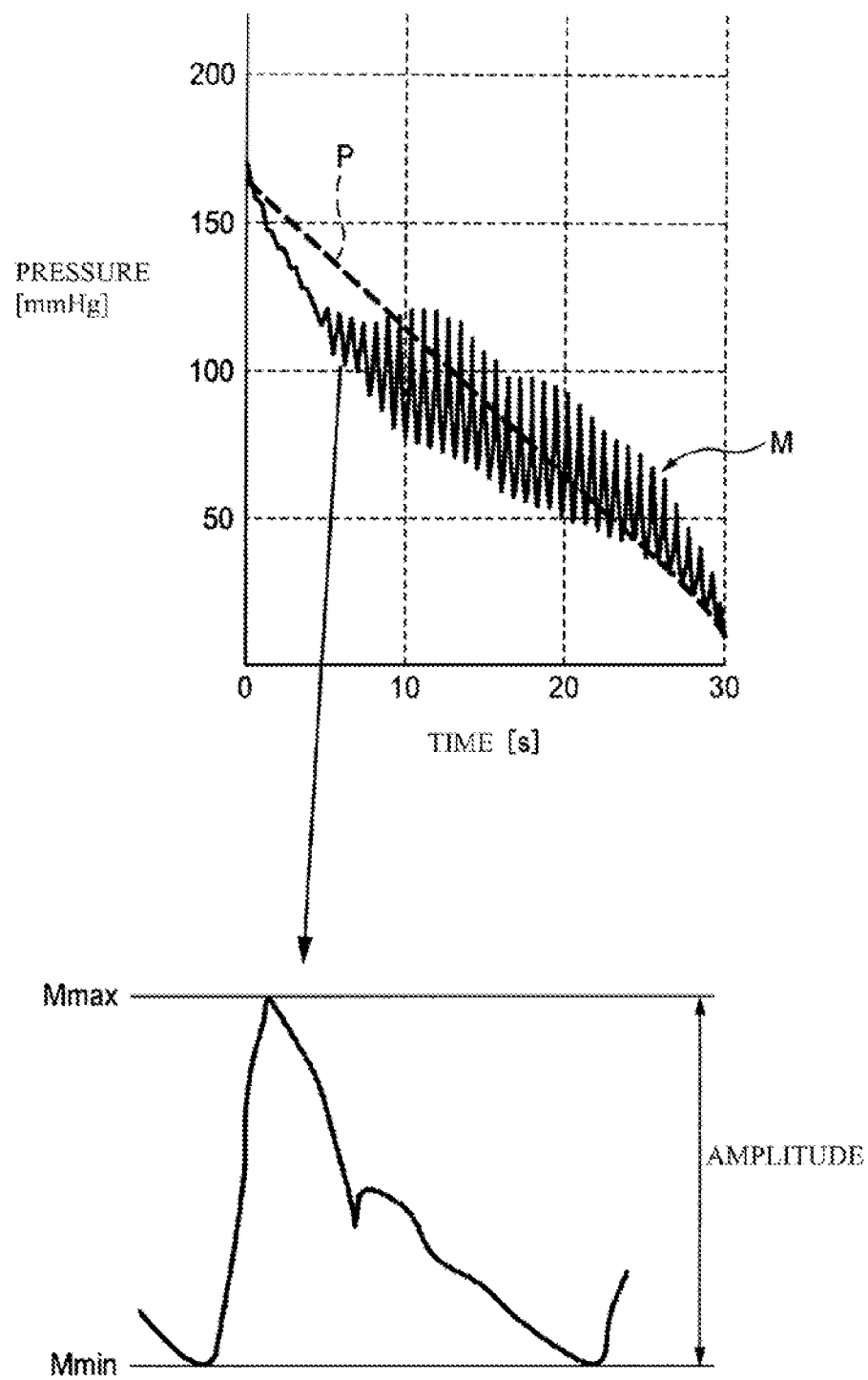
FIG. 16 is a diagram illustrating an example of a change in a pressing force applied to a wrist and a change in a pressure pulse wave detected by an optimum pressure detection element.

FIG. 16 is a diagram illustrating an example of a change in the pressing force applied to the radial artery T and a change in the pressure pulse wave detected by the optimum pressure detection element. In FIG. 16, the straight line denoted by the reference sign P indicates the pressing force, and the waveform denoted by the reference sign M represents the pressure pulse wave. An enlarged view of one pressure pulse wave is illustrated in a lower portion of FIG. 16.

As shown in FIG. 16, in the pressure pulse wave, the pressure at a rising point is referred to as a minimum value Mmin, and the pressure at a falling point is referred to as a maximum value Mmax. The amplitude of a pressure pulse wave is a value obtained by subtracting the minimum value Mmin from the maximum value Mmax. The maximum value Mmax and the minimum value Mmin are each a piece of information for specifying the shape of a pressure pulse wave.

As shown in FIG. 16, when the pressing force starts to decrease and the blocking state of the radial artery T is released, the amplitude of the pressure pulse wave detected by the optimum pressure detection element suddenly increases, and thereafter changes as shown in the diagram according to the decrease in the pressing force. The control unit 12 generates, in step S10, the pulse wave envelope data as shown in FIG. 17 from the relationship between the pressing force and the pressure pulse waves shown in FIG. 16.

Figure 17:
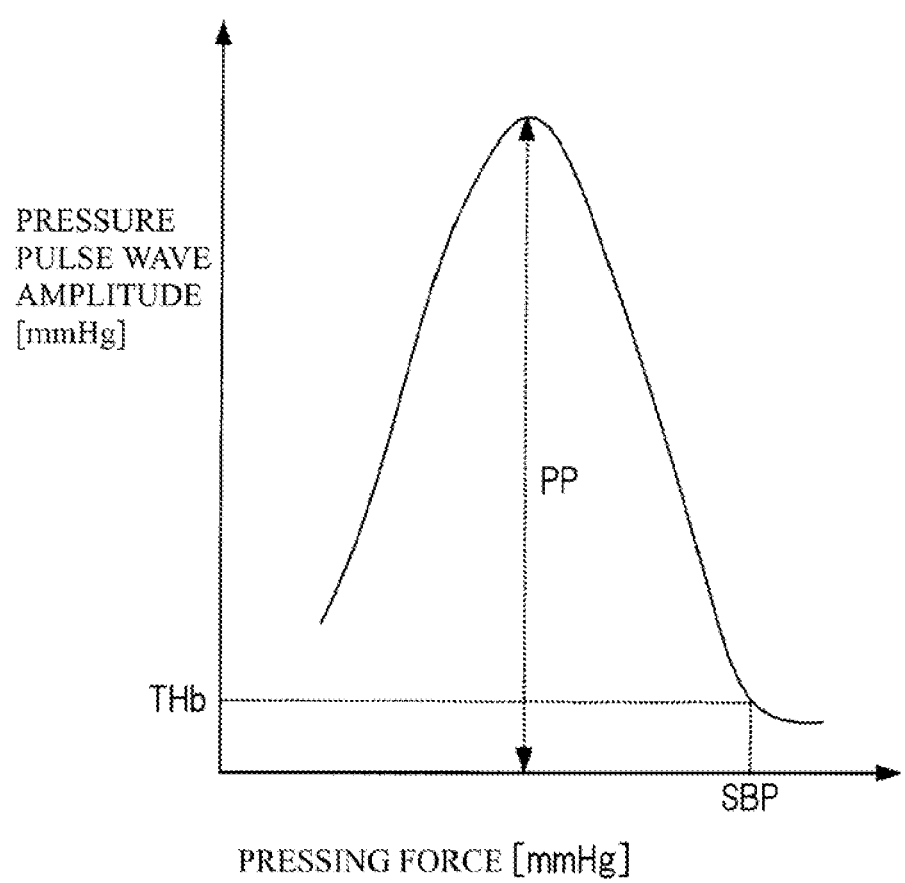
FIG. 17 is a diagram illustrating an example of pulse wave envelope data.

The control unit 12, upon generating the pulse wave envelope data shown in FIG. 17, calculates the SBP and DBP from the generated pulse wave envelope data (step S11).

For example, the control unit 12 determines, as the SBP, the pressing force at the time when the amplitude of the pressure pulse wave starts to quickly increase after the pressing force starts to decrease, that is, the pressing force at the time when, after the pressing force starts to decrease, the amplitude of the pressure pulse wave detected by the optimum pressure detection element first exceeds the threshold value THb, which indicates that the artery is no longer blocked, in the pulse wave envelope shown in FIG. 17. Alternatively, the control unit 12 calculates a difference between two adjacent amplitude values in the pulse wave envelope data, and determines the pressing force at the time when this difference has exceeded a threshold value as the SBP.

Furthermore, the control unit 12 defines the maximum value of the amplitude of the pressure pulse wave in the pulse wave envelope shown in FIG. 17 as a pulse pressure (PP), and calculates the DBP using the obtained SBP and PP and a relational expression SBP−DBP=PP.

After step S11, the control unit 12 generates calibration data to be used when continuous blood pressure measurement is performed using a maximum value Mmax and a minimum value Mmin of any of the pressure pulse waves (a pressure pulse wave having a maximum amplitude, for example) detected by the optimum pressure detection element that has been determined during a deflation process in step S9 and the SBP and DBP calculated in step S11, and stores the calibration data in the memory 15 (step S12).

The following relation holds, $$SBP = a \times M\text{max} + b \quad (1)$$

$$DBP = a \times M\text{min} + b \quad (2),$$

where a is a slope of a linear function, and b is an intercept of the linear function.

The control unit 12 substitutes the SBP and DBP obtained in step S11, and the maximum value Mmax and minimum value Mmin of the pressure pulse wave having the maximum amplitude in the pulse wave envelope in FIG. 17 into Equations (1) and (2), and calculates the slope a and the intercept b. Then, the control unit 12 stores the calculated coefficients a and b and Equations (1) and (2) into the memory 15 as the calibration data.

Figure 18:
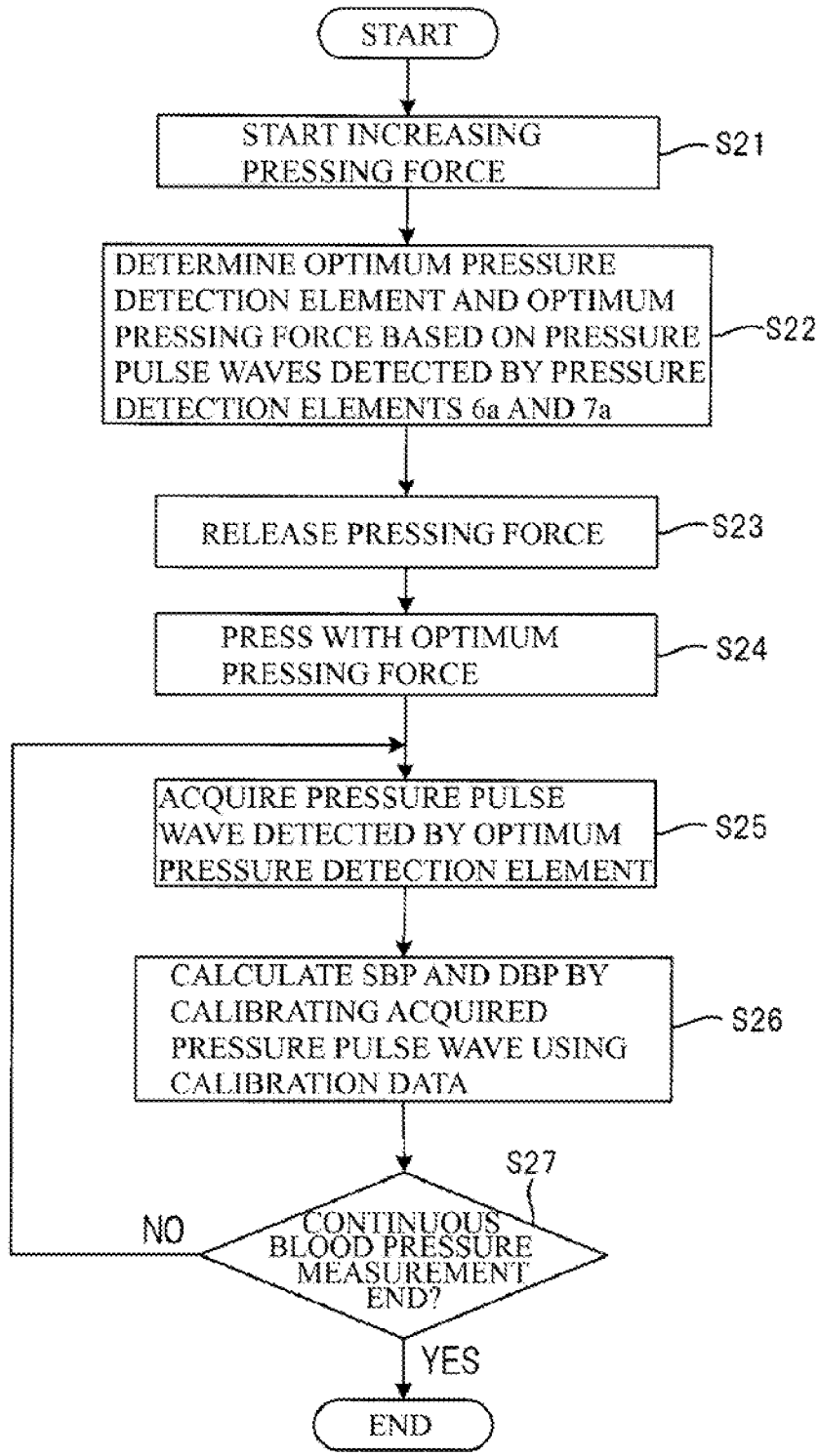
FIG. 18 is a flowchart for describing a continuous blood pressure measurement operation of the blood pressure measurement apparatus of the present embodiment in the continuous blood pressure measurement mode.

FIG. 18 is a flowchart for describing a continuous blood pressure measurement operation of the blood pressure measurement apparatus of the present embodiment in the continuous blood pressure measurement mode.

After the calibration data is generated in the flow shown in FIG. 12, the control unit 12 controls the air bladder drive unit 11 so as to increase the internal pressure of the air bladder 2 such that the pressing force applied to the radial artery T by the rotation control member 5 is increased (step S21).

Next, the control unit 12 determines the pressure detection element that has detected the pressure pulse wave having the maximum amplitude during the process of increasing the pressing force, out of the pressure detection elements 6a and 7a, as the optimum pressure detection element. Also, the control unit 12 determines the internal pressure of the air bladder 2 at the time when the pressure pulse wave having the maximum amplitude was detected as the optimum pressing force (step S22).

Next, the control unit 12 releases the internal pressure of the air bladder 2 so as to return to the initial state (step S23), thereafter, increases the internal pressure of the air bladder 2 to the optimum pressing force determined in step S22, and keeps this optimum pressing force (step S24).

Next, the control unit 12, in a state in which the sensor unit 6 is pressed toward the radial artery T with the optimum pressing force, acquires a pressure pulse wave detected by the optimum pressure detection element determined in step S22 (step S25).

Then, the control unit 12 calibrates the acquired one pressure pulse wave using the calibration data generated in step S12 in FIG. 12, and calculates the SBP and DBP (step S26).

Specifically, the control unit 12 substitutes the maximum value Mmax of the pressure pulse wave acquired in step S25 and the coefficients a and b calculated in step S12 into above-described Equation (1) so as to calculate the SBP, and substitutes the minimum value Mmin of the pressure pulse wave acquired in step S25 and the coefficients a and b calculated in step S12 into above-described Equation (2) so as to calculate the DBP. The control unit 12 displays the calculated SBP and DBP in the display unit 13, for example, so as to notify a user thereof.

If an instruction to end the continuous blood pressure measurement has been received (step S27: YES), the control unit 12 ends the processing, and if the end instruction has not been received (step S27: NO), the control unit 12 returns the processing to step S25.

As described above, according to the blood pressure measurement apparatus of the present embodiment, the sensor fixing surface 3c on which the sensor unit 6 is fixed can rotate about each of two axes (first axis X and second axis Y) that are orthogonal to the pressing direction of the sensor unit 6. Therefore, as a result of the operations illustrated in FIG. 12 being performed, the detection accuracy of the pressure pulse wave can be improved, and the calculation accuracy of the blood pressure information serving as the bodily information that is calculated based on the pressure pulse wave can be improved.

The rotation of the sensor fixing surface 3c is realized by the ring cam 40 being rotated by one ultrasonic motor 46. Therefore, the mechanism for rotating the sensor fixing surface 3c is simplified and made compact, and as a result, the size and the cost of the pressure pulse wave measurement unit 100 can be reduced.

Also, the rotation of the sensor fixing surface 3c is realized by the movement of the cam faces of the ring cam 40 relative to the contact members of the sensor table 3. Therefore, the motion sound of the sensor fixing surface 3c when rotated can be reduced relative to the case where the sensor fixing surface 3c is rotated using a gear or the like.

Also, since the sensor fixing surface 3c is rotated by a rotational motion of the ring cam 40, the rotational torque needed to rotate the ring cam 40 can be reduced. Therefore, the power consumption when the sensor fixing surface 3c is rotated can be reduced, and the battery life of the blood pressure measurement apparatus can be improved. Also, as a result of using the ring cam 40, the size of the actuator for rotating the ring cam 40 can be reduced, and as a result, the size of the pressure pulse wave measurement unit 100 can be reduced.

The rotation of the sensor fixing surface 3c about the second axis Y is performed so as to prevent the detection accuracy of the pressure pulse wave from decreasing as a result of the radial artery T moving in the direction B. Therefore, with respect to the rotation of the sensor fixing surface 3c about the second axis Y, the sensor fixing surface 3c need only be rotated to such a degree that the position of the radial artery T can be changed, and the rotation angle need not be finely controlled.

On the other hand, the rotation of the sensor fixing surface 3c about the first axis X is performed such that the sensor fixing surface 3c is parallel to the radial artery T. The change in the depth of the radial artery T in the running direction varies from person to person, and the depth of the radial artery T may increase due to the pressing force of the sensor unit 6. Therefore, in order to bring the sensor fixing surface 3c in parallel to the radial artery T, it is preferable that the rotation angle of the sensor fixing surface 3c about the second axis Y can be finely controlled.

According to these reasons, in the blood pressure measurement apparatus of the present embodiment, the rotation angle of the sensor fixing surface 3c about the second axis Y is controlled to one of three values, namely $-5°$, $0°$, $+5'$, and the rotation angle of the sensor fixing surface 3c about the first axis X is controlled to any value in the range from $-5°$ to $+5°$. The rising and falling patterns of the cam faces of the ring cam 40 for realizing such control are not complex, as shown in FIG. 9. Therefore, the design cost of the pressure pulse wave measurement unit 100 can be reduced, and the manufacturing cost thereof can be reduced.

Note that the specific values of the three rotation angles ($-5°$, $0°$, $+5°$) about the second axis Y, and the values (from $-5°$ to $+5°$) that the rotation angle about the first axis X can take are shown as merely an example, and are not limited thereto. For example, the inclinations of the cam faces may be designed such that the combinations of each of three rotation angles ($-10°$, $0°$, $+10°$) about the second axis Y and all values (from $-10°$ to $+10°$) that the rotation angle about the first axis X can take can be realized.

Note that, if the rising and falling patterns of the cam faces of the ring cam 40 are devised, the rotation angle of the sensor fixing surface 3c about the second axis Y can be controlled to any value in a range from $-5°$ to $+5°$.

In the above description, the rotation control member 5 changes the rotation angle of the sensor fixing surface 3c about the first axis X in the range from $-5°$ to $+5°$ in a state in which the rotation angle of the sensor fixing surface 3c about the second axis Y is fixed to each of three values. However, the number of required rotation angles about the second axis Y may be two or more, considering the detection accuracy of the pressure pulse wave.

That is, the rotation control member 5 may be configured to change the rotation angle of the sensor unit 6 fixed to the sensor fixing surface 3c about the first axis X in a range from $-5°$ to $+5°$ in a state in which the rotation angle of the sensor unit 6 about the second axis Y is fixed at each of two or four or more values. Note that because the design of the ring cam 40 becomes complicated if the number of rotation angles about the second axis Y is increased too much, the number of rotation angles about the second axis Y is preferably three or five.

As described above, since the rotation angle of the sensor fixing surface 3c about the first axis X needs to be finely controlled, the error of the rotation angle is preferably small.

In the rotation control member 5, since the first cam face 40a is located farthest from the rotation axis J1, the distance that the first contact member 3d moves on the first cam face 40a is larger than those on the other cam faces. Therefore, the shift amount of the rotation angle of the sensor fixing surface 3c about the first axis X when the contact position between the first cam face 40a and the first contact member 3d shifts from a desired position is smaller than the shift amount of the sensor fixing surface 3c about the second axis Y when the contact position between the second cam face 40b and the second contact member 3e shifts from a desired position. Accordingly, as a result of the first cam face 40a being located farthest from the rotation axis J1, the error of the rotation angle of the sensor fixing surface 3c about the first axis X can be reduced, and the rotation of the sensor table 3 can be controlled with high accuracy.

Also, in the pressure pulse wave measurement unit 100, the sensor table 3 is designed such that only the first contact member 3d overlaps the first cam face 40a, as shown in FIG. 8. According to this configuration, there is no concern that a portion of the sensor table 3 other than the first contact member 3d will come into contact with the first cam face 40a. Therefore, the distance between an end surface of the sensor table on a side opposite to the sensor fixing surface 3c in the state shown in FIG. 8 and an end surface of the ring cam 40 on a sensor table 3 side can be reduced. Accordingly, the size of the pressure pulse wave measurement unit 100 can be reduced.

Also, in the pressure pulse wave measurement unit 100, as shown in FIG. 3, the direction (direction B) along which the pressure detection elements of the element columns 60 and 70 included in the sensor unit 6 that is arranged on the sensor fixing surface 3c are arranged side by side substantially matches the direction connecting the first contact member 3d and the rotation axis J1 when the sensor fixing surface 3c is viewed in a direction perpendicular to the sensor fixing surface 3c.

Here, the first contact member 3d is a point of action that is located farthest from the rotation axis J1, which passes through a supporting point of the sensor table 3. Therefore, as a result of matching the direction connecting this supporting point and the point of action with the longitudinal direction of the sensor unit 6, the orientation of the sensor table 3 can be stabilized, and the rotation of the sensor table 3 can be controlled with high accuracy.

Also, the pressure pulse wave measurement unit 100 is configured such that the cam faces of the ring cam 40 extend along the circumference of a circle centered about the rotation axis J. According to this configuration, the design of the ring cam 40 can be facilitated, and the manufacturing cost of the pressure pulse wave measurement unit 100 can be reduced.

Also, the pressure pulse wave measurement unit 100 is configured such that the third cam face 40*c* is provided on the ring cam 40, and the third contact member 3*f* is provided in the sensor table 3. According to this configuration, the sensor table 3 is supported by the three contact members and the base 48. Accordingly, the orientation of the sensor table 3 can be stabilized, and the rotation of the sensor table 3 can be controlled with high accuracy.

Note that the third cam face 40*c* of the ring cam 40 and the third contact member 3*f* of the sensor table 3 can be omitted. Even in a case of omitting these members, the sensor table 3 is supported by the two contact members and the base 48, and as a result, the orientation of the sensor table 3 can be stabilized.

Hereinafter, modified examples of the pressure pulse wave measurement unit 100 will be described.

The rotation control member 5 may be configured so as to rotate the sensor unit 6 about each of the first axis X and the second axis Y by rotating the sensor table 3 without rotating the ring cam 40. In the case where this configuration is adopted, a mechanism may be adopted in which the sensor unit 6 is not fixed to the sensor fixing surface 3*c* of the sensor table 3 and the sensor surface 6*b* of the sensor unit 6 inclines following the inclination of the sensor fixing surface 3*c* in a state in which the direction along which the element columns 60 and 70 of the sensor unit 6 extend is fixed.

The rotation control member 5 may be configured such that the end surface of the ring cam 40 on a side opposite to the sensor table 3 is a flat plane, the ring cam 40 cannot be rotated, the sensor unit 6 is fixed to this flat plane, and the sensor table 3 can be rotated about the rotation axis J1 by a motor. According to this configuration as well, the sensor unit 6 can be rotated about each of the first axis X and the second axis Y by rotating the sensor table 3.

In the rotation control member 5, a motor other than the ultrasonic motor may be used as the motor for rotating the ring cam 40. Since the ring cam 40 has a ring shape, as a result of using a ring-type motor, the design of the rotation control member 5 can be facilitated.

The rotation control member 5 may be configured to have cam faces that are formed such that the sensor fixing surface 3*c* rotates about the second axis Y due to the movement of the first cam face 40*a* relative to the first contact member 3*d*, and the sensor fixing surface 3*c* rotates about the first axis X due to the movement of the second cam face 40*b* relative to the second contact member 3*e*. Also, the shape of each cam face of the ring cam 40 is not limited to a shape extending along the circumferential direction, and any shape may be adopted as long as the rotation angle of the sensor fixing surface 3*c* can be set to a desired value.

As described above, the following items are disclosed in the present specification.

The disclosed pressure pulse wave measurement apparatus includes: a sensor unit in which an element column including a plurality of pressure detection elements that are arranged side by side in one direction is formed; a pressing unit configured to press the sensor unit against a body surface of a living body; and a rotation control member configured to rotate the sensor unit about each of two axes that are orthogonal to a pressing direction of the pressing unit. The rotation control member includes a first member and a second member that are relatively rotated about a rotation axis extending in the pressing direction, and the first member and the second member both include a motion conversion mechanism for converting a rotational motion realized by the first member and the second member being relatively rotated, into a rotational motion of the sensor unit about each of the two axes.

In the disclosed pressure pulse wave measurement apparatus, the pressing unit presses the sensor unit against the body surface in a state in which a direction in which the plurality of pressure detection elements are arranged side by side intersects a direction in which an artery under the body surface extends, and the two axes are a first axis extending in the direction in which the plurality of pressure detection elements are arranged side by side and a second axis extending in a direction orthogonal to the direction.

In the disclosed pressure pulse wave measurement apparatus, in respective states in which a rotation angle of the sensor unit about the second axis is fixed at a respective plurality of values, the rotation control member changes a rotation angle of the sensor unit about the first axis over a range of angles by which the sensor unit can rotate about the first axis.

In the disclosed pressure pulse wave measurement apparatus, the second member includes a first cam face and a second cam face that are formed on an end surface in the pressing direction, the first cam face and the second cam face each extend along a circumference of a circle centered about the rotation axis, the first cam face is to located farther from the rotation axis relative to the second cam face, a first contact member that comes into contact with the first cam face and a second contact member that comes into contact with the second cam face are formed in the first member, the motion conversion mechanism is constituted by the first cam face, the second cam face, the first contact member, and the second contact member, and the rotation control member rotates the sensor unit about the first axis as a result of a relative movement of the first cam face and the first contact member caused by the first member and the second member being relatively rotated, and rotates the sensor unit about the second axis as a result of a relative movement of the second cam face and the second contact member caused by the first member and the second member being relatively rotated.

In the disclosed pressure pulse wave measurement apparatus, the sensor unit is fixed to an end surface of the first member in the pressing direction, and the direction in which the plurality of pressure detection elements of the element column included in the sensor unit are arranged side by side matches a direction connecting the first contact member and the rotation axis in a state in which the end surface of the first member on which the sensor unit is fixed is viewed in a direction perpendicular to the end surface.

In the disclosed pressure pulse wave measurement apparatus, the sensor unit is fixed to an end surface of the first member in the pressing direction, and the first member is configured such that only the first contact member overlaps the first cam face, in plan view viewed in a direction perpendicular to the end surface on which the sensor unit is fixed, in a state in which the direction perpendicular to the end surface matches the pressing direction.

In the disclosed pressure pulse wave measurement apparatus, the second member includes a first cam face and a second cam face that are formed on an end surface in the pressing direction, a first contact member that comes into contact with the first cam face and a second contact member that comes into contact with the second cam face are formed in the first member, and the motion conversion mechanism is to constituted by the first cam face, the second cam face, the first contact member, and the second contact member.

In the disclosed pressure pulse wave measurement apparatus, the first cam face and the second cam face each extend along a circumference of a circle centered about the rotation axis, and the first cam face is located farther from the rotation axis relative to the second cam face.

In the disclosed pressure pulse wave measurement apparatus, the sensor unit is fixed to an end surface of the first member in the pressing direction, and the direction in which the plurality of pressure detection elements of the element column included in the sensor unit are arranged side by side matches a direction connecting the first contact member and the rotation axis in a state in which the end surface of the first member on which the sensor unit is fixed is viewed in a direction perpendicular to the end surface.

In the disclosed pressure pulse wave measurement apparatus, the sensor unit is fixed to an end surface of the first member in the pressing direction, and the first member is configured such that only the first contact member overlaps the first cam face, in plan view viewed in a direction perpendicular to the end surface on which the sensor unit is fixed, in a state in which the direction perpendicular to the end surface matches the pressing direction.

In the disclosed pressure pulse wave measurement apparatus, the second member further includes a third cam face formed on the end surface in the pressing direction, a third contact member that comes into contact with the third cam face is further formed in the first member, and the motion conversion mechanism is constituted by the first cam face, the second cam face, the third cam face, the first contact member, the second contact member, and the third contact member.

In the disclosed pressure pulse wave measurement apparatus, the sensor unit includes a plurality of the element columns that are arranged side by side in a direction orthogonal to the one direction.

The disclosed bodily information measurement apparatus includes the above-described pressure pulse wave measurement apparatus; and a bodily information calculation unit configured to calculate bodily information based on a pressure pulse wave detected by a pressure detection element of the sensor unit.

A pressure pulse wave measurement apparatus of the present invention includes: a sensor unit in which an element column including a plurality of pressure detection elements that are arranged side by side in one direction is formed; a pressing unit configured to press the sensor unit against a body surface of a living body; and a rotation control member configured to rotate the sensor unit about each of two axes that are orthogonal to a pressing direction of the pressing unit. The rotation control member includes a first member and a second member that are relatively rotated about a rotation axis extending in the pressing direction. The first member and the second member both include a motion conversion mechanism for converting a rotational motion realized by the first member and the second member being relatively rotated into a rotational motion of the sensor unit about each of the two axes.

The bodily information measurement apparatus of the present invention includes: the pressure pulse wave measurement apparatus; and a bodily information calculation unit configured to calculate bodily information based on a pressure pulse wave detected by a pressure detection element of the sensor unit.

According to the present invention, it is possible to provide a pressure pulse wave measurement apparatus in which the state of contact between a sensor unit, which is brought into contact with a body region for use, and the body region can be flexibly changed so as to improve the measurement accuracy of a pressure pulse wave, and a bodily information measurement apparatus including the pressure pulse wave measurement apparatus.

INDUSTRIAL APPLICABILITY

According to the present invention, a pressure pulse wave measurement apparatus can be provided in which the state of contact between a sensor unit, which is brought into contact with a body region for use, and the body region can be flexibly changed so as to improve the measurement accuracy of the pressure pulse wave.

Although the present invention has been described above by means of specific embodiments, the present invention is not limited to the embodiments, and various modifications are possible without departing from the technical gist of the disclosed invention.

REFERENCE SIGNS LIST

100 Pressure pulse wave measurement unit
5 Rotation control member
6 Sensor unit
60, 70 Element column
3 Sensor table
3c Sensor fixing surface
3d First contact member
3e Second contact member
40 Ring cam
40a First cam face
40b Second cam face
46 Ultrasonic motor
48 Base

The invention claimed is:

1. A pressure pulse wave measurement apparatus comprising:
a sensor unit which includes an element column including a plurality of pressure detection elements that are arranged side by side in one direction;
a presser configured to press the sensor unit against a body surface of a living body; and
a rotator configured to rotate the sensor unit about each of two axes that are orthogonal to a pressing direction of the presser,
wherein the rotator includes a first rotor and a second rotor that are configured to be relatively rotated about a rotation axis extending in the pressing direction, and
the first rotor and the second rotor both include a motion converter for converting a rotational motion realized by the first rotor and the second rotor being relatively rotated, into a rotational motion of the sensor unit about each of the two axes.

2. The pressure pulse wave measurement apparatus according to claim 1,
wherein the presser presses the sensor unit against the body surface in a state in which a direction in which the plurality of pressure detection elements are arranged side by side intersects a direction in which an artery under the body surface extends, and the two axes are a first axis extending in the direction in which the plurality of pressure detection elements are arranged side by side and a second axis extending in a direction orthogonal to the direction.

3. The pressure pulse wave measurement apparatus according to claim 2, wherein in respective states in which a rotation angle of the sensor unit about the second axis is fixed at a respective plurality of values, the rotator changes a rotation angle of the sensor unit about the first axis over a range of angles by which the sensor unit can rotate about the first axis.

4. The pressure pulse wave measurement apparatus according to claim 2, wherein the second rotor includes a first cam face and a second cam face that are formed on an end surface in the pressing direction, the first cam face and the second cam face each extend along a circumference of a circle centered about the rotation axis, the first cam face is located farther from the rotation axis relative to the second cam face, a first contact member that comes into contact with the first cam face and a second contact member that comes into contact with the second cam face are formed in the first rotor, the motion converter is constituted by the first cam face, the second cam face, the first contact member, and the second contact member, and the rotator rotates the sensor unit about the first axis as a result of a relative movement of the first cam face and the first contact member caused by the first rotor and the second rotor being relatively rotated, and rotates the sensor unit about the second axis as a result of a relative movement of the second cam face and the second contact member caused by the first rotor and the second rotor being relatively rotated.

5. The pressure pulse wave measurement apparatus according to claim 4, wherein the sensor unit is fixed to an end surface of the first rotor in the pressing direction, and the direction in which the plurality of pressure detection elements of the element column included in the sensor unit are arranged side by side matches a direction connecting the first contact member and the rotation axis in a state in which the end surface of the first rotor on which the sensor unit is fixed is viewed in a direction perpendicular to the end surface.

6. The pressure pulse wave measurement apparatus according to claim 4, wherein the sensor unit is fixed to an end surface of the first rotor in the pressing direction, and the first rotor is configured such that only the first contact member overlaps the first cam face, in plan view viewed in a direction perpendicular to the end surface on which the sensor unit is fixed, in a state in which the direction perpendicular to the end surface matches the pressing direction.

7. The pressure pulse wave measurement apparatus according to claim 1, wherein the second rotor includes a first cam face and a second cam face that are formed on an end surface in the pressing direction, a first contact member that comes into contact with the first cam face and a second contact member that comes into contact with the second cam face are formed in the first rotor, and the motion converter is constituted by the first cam face, the second cam face, the first contact member, and the second contact member.

8. The pressure pulse wave measurement apparatus according to claim 7, wherein the first cam face and the second cam face each extend along a circumference of a circle centered about the rotation axis, and the first cam face is located farther from the rotation axis relative to the second cam face.

9. The pressure pulse wave measurement apparatus according to claim 8, wherein the sensor unit is fixed to an end surface of the first rotor in the pressing direction, and a direction in which the plurality of pressure detection elements of the element column included in the sensor unit are arranged side by side matches a direction connecting the first contact member and the rotation axis in a state in which the end surface of the first rotor on which the sensor unit is fixed is viewed in a direction perpendicular to the end surface.

10. The pressure pulse wave measurement apparatus according to claim 7, wherein the sensor unit is fixed to an end surface of the first rotor in the pressing direction, and the first rotor is configured such that only the first contact member overlaps the first cam face, in plan view viewed in a direction perpendicular to the end surface on which the sensor unit is fixed, in a state in which the direction perpendicular to the end surface matches the pressing direction.

11. The pressure pulse wave measurement apparatus according to claim 4, wherein the second rotor further includes a third cam face formed on the end surface in the pressing direction, a third contact member that comes into contact with the third cam face is further formed in the first rotor, and the motion converter is constituted by the first cam face, the second cam face, the third cam face, the first contact member, the second contact member, and the third contact member.

12. The pressure pulse wave measurement apparatus according to claim 1, wherein the sensor unit includes a plurality of the element columns that are arranged side by side in a direction orthogonal to the one direction.

13. A bodily information measurement apparatus comprising:

the pressure pulse wave measurement apparatus according to claim 1; and a bodily information calculation unit configured to calculate bodily information based on a pressure pulse wave detected by a pressure detection element of the sensor unit.

* * * * *